US009499526B2

(12) United States Patent
Kandula

(10) Patent No.: US 9,499,526 B2
(45) Date of Patent: Nov. 22, 2016

(54) COMPOSITIONS AND METHODS FOR THE TREATMENT OF NEUROLOGIC DISEASES

(71) Applicant: Mahesh Kandula, Andhra Pradesh (IN)

(72) Inventor: Mahesh Kandula, Andhra Pradesh (IN)

(73) Assignee: CELLIX BIO PRIVATE LIMITED, Hyderabad, Telangana (IN)

(*) Notice: Subject to any disclaimer, the term of this patent is extended or adjusted under 35 U.S.C. 154(b) by 0 days.

(21) Appl. No.: 14/399,174

(22) PCT Filed: Apr. 19, 2013

(86) PCT No.: PCT/IB2013/053122
§ 371 (c)(1),
(2) Date: Nov. 6, 2014

(87) PCT Pub. No.: WO2013/168033
PCT Pub. Date: Nov. 14, 2013

(65) Prior Publication Data
US 2015/0218136 A1    Aug. 6, 2015

(30) Foreign Application Priority Data
May 10, 2012 (IN) .......................... 1862/CHE/2012

(51) Int. Cl.
*C07D 409/12* (2006.01)
*C07D 333/20* (2006.01)
*C07D 333/24* (2006.01)
*A61P 25/16* (2006.01)
*A61K 31/381* (2006.01)

(52) U.S. Cl.
CPC ........... *C07D 409/12* (2013.01); *C07D 333/20* (2013.01); *C07D 333/24* (2013.01)

(58) Field of Classification Search
CPC .... C07D 333/20; A61P 25/16; A61K 31/381
USPC ...................................................... 514/238.8
See application file for complete search history.

(56) References Cited

U.S. PATENT DOCUMENTS

| 2,807,644 | A | 9/1957 | Moore et al. |
| 4,011,342 | A | 3/1977 | Schwartz et al. |
| 4,404,366 | A | 9/1983 | Boguslaski et al. |
| 4,412,992 | A | 11/1983 | Chan |
| 4,440,763 | A | 4/1984 | Lover |
| 4,550,109 | A | 10/1985 | Folkers et al. |
| 4,564,628 | A | 1/1986 | Horn |
| 4,778,794 | A | 10/1988 | Naruse et al. |
| 4,873,259 | A | 10/1989 | Summers, Jr. et al. |
| 4,920,122 | A | 4/1990 | Naruse et al. |
| 4,963,590 | A | 10/1990 | Backstrom et al. |
| 5,013,727 | A | 5/1991 | Halskov |
| 5,104,887 | A | 4/1992 | Schoenwald et al. |
| 5,120,738 | A | 6/1992 | Ikawa et al. |
| 5,242,937 | A | 9/1993 | Pierce, Jr. |
| 5,352,703 | A | 10/1994 | Quadro |
| 5,719,168 | A | 2/1998 | Laurent |
| 5,830,907 | A | 11/1998 | Doble et al. |
| 5,886,001 | A | 3/1999 | Schmidhammer |
| 6,156,777 | A | 12/2000 | Hall et al. |
| 6,414,008 | B1 | 7/2002 | Hauel et al. |
| 6,602,915 | B2 | 8/2003 | Uhrich |
| 6,610,708 | B1 | 8/2003 | Asai et al. |
| 6,613,802 | B1 | 9/2003 | Luskey et al. |
| 7,101,912 | B2 | 9/2006 | Xiang et al. |
| 7,544,834 | B2 | 6/2009 | Sumikawa et al. |
| 7,645,767 | B2 | 1/2010 | Singh et al. |
| 7,910,568 | B2 | 3/2011 | Wallace et al. |
| 8,025,897 | B2 | 9/2011 | Bunick et al. |
| 8,778,991 | B2 | 7/2014 | Gangakhedkar et al. |
| 2003/0139437 | A1 | 7/2003 | Dobrozsi et al. |
| 2003/0220468 | A1 | 11/2003 | Lai et al. |
| 2003/0232867 | A1 | 12/2003 | Kobayashi et al. |
| 2004/0010038 | A1 | 1/2004 | Blaugrund et al. |
| 2004/0048924 | A1 | 3/2004 | Bunick et al. |
| 2004/0106576 | A1 | 6/2004 | Jerussi et al. |
| 2004/0170680 | A1 | 9/2004 | Oshlack et al. |
| 2004/0215004 | A1 | 10/2004 | Berkner et al. |
| 2004/0259953 | A1 | 12/2004 | Deregnaucourt et al. |
| 2005/0020665 | A1 | 1/2005 | Neu |

(Continued)

FOREIGN PATENT DOCUMENTS

CA    1199916 A1    1/1986
CN    1224610 A     8/1999

(Continued)

OTHER PUBLICATIONS

Chemical Abstracts STN Database Record for RN 1369499-25-1, dated Apr. 17, 2012.*
Den Daas; Naunyn-Schmiedeberg's Arch Pharmacol 1990, 342, 655-659.*
Den Daas; Naunyn-Schmiedeberg's Arch Pharmacol, 1990, 341, 186-191.*
Jansen; Naunyn-Schmiedeberg's Arch Pharmacol, 1991, 343, 134-142.*
Den Daas; Naunyn-Schmiedeberg's Arch Pharmaco1,1990, 341, 186-191.*
Denivelle; Compt. Rend. 1952, 235, 1514-1516; Abstract from CAPLUS Database.*
Yu; European Journal of Medicinal Chemistry 2011, 46, 5833-5837.*
Clark; "Peroxides and Peroxide Forming Compounds" Texas A & M University Chemical Safety Publication, 2000.*
"Amidines and related compounds. 6. Studies on structure-activity relationships of antihypertensive and antisecretory agents related to clonidine", US National Library of Medicine National Institutes of HealthSearch database, Jan. 1975, by Jen T et al. (p. 1) http://www.ncbi.nlm.nih.gov/pubmed/234014?report=abstract.

(Continued)

Primary Examiner — Noble Jarrell
Assistant Examiner — Daniel Carcanague
(74) Attorney, Agent, or Firm — Raj Abhyanker, P.C.

(57) ABSTRACT

The invention relates to the compounds of formula I or its pharmaceutical acceptable salts, as well as polymorphs, solvates, enantiomers, stereoisomers and hydrates thereof. The pharmaceutical compositions comprising an effective amount of compounds of formula I, and methods for the treatment of neurologic diseases may be formulated for oral, buccal, rectal, topical, transdermal, transmucosal, intravenous, parenteral administration, syrup, or injection. Such compositions may be used to treatment of depression, Alzheimer's disease, multiple sclerosis, Batten disease, multiple sclerosis, Parkinson's disease (PD) and restless legs syndrome (RLS).

10 Claims, No Drawings

(56) References Cited

U.S. PATENT DOCUMENTS

| | | |
|---|---|---|
| 2005/0106248 A1 | 5/2005 | Dixit et al. |
| 2005/0244486 A1 | 11/2005 | Caldwell et al. |
| 2006/0014837 A1 | 1/2006 | Deregnaucourt et al. |
| 2006/0057644 A1 | 3/2006 | Kelly et al. |
| 2006/0058373 A1 | 3/2006 | Abdel-Magid et al. |
| 2006/0142566 A1 | 6/2006 | Mathes et al. |
| 2006/0270635 A1 | 11/2006 | Wallace et al. |
| 2006/0270706 A1 | 11/2006 | Kimura et al. |
| 2007/0259930 A1 | 11/2007 | Bozik et al. |
| 2008/0020996 A1 | 1/2008 | Singh et al. |
| 2008/0058362 A1 | 3/2008 | Singh et al. |
| 2008/0064743 A1 | 3/2008 | Shah et al. |
| 2008/0132578 A1 | 6/2008 | Jerussi et al. |
| 2008/0207564 A1 | 8/2008 | Wallace et al. |
| 2008/0221111 A1 | 9/2008 | Hesslinger et al. |
| 2008/0227985 A1 | 9/2008 | Raje et al. |
| 2008/0262053 A1 | 10/2008 | Reess |
| 2008/0269166 A2 | 10/2008 | Jerussi et al. |
| 2008/0280936 A1 | 11/2008 | Tung |
| 2008/0319222 A1 | 12/2008 | Sutton |
| 2009/0075942 A1 | 3/2009 | Czarnik |
| 2009/0118365 A1 | 5/2009 | Benson, III et al. |
| 2009/0131535 A1 | 5/2009 | Blaugrund et al. |
| 2009/0326062 A1 | 12/2009 | Palomo Nicolau et al. |
| 2010/0004255 A1 | 1/2010 | Belardinelli et al. |
| 2010/0016328 A1 | 1/2010 | Kakkis et al. |
| 2010/0081713 A1 | 4/2010 | Sharma et al. |
| 2010/0316712 A1 | 12/2010 | Nangia et al. |
| 2011/0021628 A1 | 1/2011 | Estrada et al. |
| 2011/0087028 A1 | 4/2011 | Hwang et al. |
| 2011/0165234 A1 | 7/2011 | Dixit et al. |
| 2011/0172240 A1 | 7/2011 | Milne et al. |
| 2011/0218180 A1 | 9/2011 | Singh et al. |
| 2011/0229561 A1 | 9/2011 | Kapoor et al. |
| 2011/0230514 A1 | 9/2011 | Tung |
| 2011/0300190 A1 | 12/2011 | Kandula |
| 2011/0313036 A1 | 12/2011 | Estrada et al. |
| 2011/0313176 A1 | 12/2011 | Khunt et al. |
| 2012/0021046 A1 | 1/2012 | Capomacchia et al. |
| 2012/0022072 A1 | 1/2012 | Kakkis et al. |
| 2012/0046272 A1 | 2/2012 | Sesha |
| 2012/0093922 A1 | 4/2012 | Manku et al. |
| 2012/0095003 A1 | 4/2012 | Gangakhedkar et al. |
| 2012/0115817 A1 | 5/2012 | Dos Santos et al. |
| 2012/0157523 A1 | 6/2012 | Gangakhedkar et al. |
| 2012/0208850 A1 | 8/2012 | Kong et al. |
| 2012/0302794 A1 | 11/2012 | Jerussi et al. |
| 2013/0065909 A1 | 3/2013 | Milne et al. |
| 2013/0190327 A1 | 7/2013 | Milne et al. |
| 2013/0217737 A1 | 8/2013 | Hasse et al. |
| 2013/0267605 A1 | 10/2013 | Scheuring et al. |
| 2014/0080815 A1 | 3/2014 | Wilhelm-Ogunbiyi et al. |
| 2014/0100372 A1 | 4/2014 | Raje et al. |
| 2014/0134753 A1 | 5/2014 | Kelly et al. |
| 2014/0155455 A1 | 6/2014 | Osterloh et al. |
| 2014/0228389 A1 | 8/2014 | Shah et al. |
| 2014/0235710 A1 | 8/2014 | Estrada et al. |

FOREIGN PATENT DOCUMENTS

| | | |
|---|---|---|
| CN | 1300213 A | 6/2001 |
| CN | 1672678 A | 9/2005 |
| CN | 1706813 A | 12/2005 |
| CN | 1248690 C | 4/2006 |
| CN | 1897935 A | 1/2007 |
| CN | 101023056 A | 8/2007 |
| CN | 101186583 A | 5/2008 |
| CN | 101202326 A | 6/2008 |
| CN | 101208326 A | 6/2008 |
| CN | 100448852 C | 1/2009 |
| CN | 101390854 A | 3/2009 |
| CN | 100548300 C | 10/2009 |
| CN | 101569618 A | 11/2009 |
| CN | 101717392 A | 6/2010 |
| CN | 101724934 A | 6/2010 |
| CN | 101921245 A | 12/2010 |
| CN | 102002053 A | 4/2011 |
| CN | 102123763 A | 7/2011 |
| CN | 102149673 A | 8/2011 |
| CN | 102336767 A | 2/2012 |
| CN | 102633799 A | 8/2012 |
| CN | 102050815 B | 4/2014 |
| EP | 0141393 A2 | 5/1985 |
| EP | 0150787 A2 | 8/1985 |
| EP | 0421441 A2 | 4/1991 |
| EP | 0934928 A1 | 8/1999 |
| EP | 1063230 A1 | 12/2000 |
| EP | 1695962 A1 | 8/2006 |
| EP | 1870395 A1 | 12/2007 |
| EP | 1889835 A1 | 2/2008 |
| EP | 1997493 A1 | 12/2008 |
| EP | 2298777 A2 | 3/2011 |
| EP | 2450039 A1 | 5/2012 |
| FR | 2722199 A1 | 1/1996 |
| GB | 1014020 A | 12/1965 |
| GB | 2116541 A | 9/1983 |
| JP | 56077259 A | 6/1981 |
| JP | S6089474 A | 5/1985 |
| RU | 2436772 C2 | 12/2011 |
| WO | 9114430 A1 | 10/1991 |
| WO | 9118865 A1 | 12/1991 |
| WO | 9305029 A1 | 3/1993 |
| WO | 9413298 A1 | 6/1994 |
| WO | 9522546 A1 | 8/1995 |
| WO | 9551464 A1 | 11/1995 |
| WO | 9822433 A1 | 5/1998 |
| WO | 9852556 A1 | 11/1998 |
| WO | 0041693 A2 | 7/2000 |
| WO | 0059851 A1 | 10/2000 |
| WO | 0122967 A1 | 4/2001 |
| WO | 0200167 A2 | 1/2002 |
| WO | 0234713 A1 | 5/2002 |
| WO | 02062332 A1 | 8/2002 |
| WO | 02087512 A2 | 11/2002 |
| WO | 03018004 A2 | 3/2003 |
| WO | 03030877 A1 | 4/2003 |
| WO | 03086391 A1 | 10/2003 |
| WO | 03087038 A1 | 10/2003 |
| WO | 03097656 A2 | 11/2003 |
| WO | 2004031155 A1 | 4/2004 |
| WO | 2004052841 A1 | 6/2004 |
| WO | 2004075886 A1 | 9/2004 |
| WO | 2004078769 A1 | 9/2004 |
| WO | 2005046575 A2 | 5/2005 |
| WO | 2005110381 A1 | 11/2005 |
| WO | 2005116086 A2 | 12/2005 |
| WO | 2006096996 A1 | 9/2006 |
| WO | 2006120176 A2 | 11/2006 |
| WO | 2006125293 A1 | 11/2006 |
| WO | 2007086493 A1 | 8/2007 |
| WO | 2007121188 A2 | 10/2007 |
| WO | 2008030567 A2 | 3/2008 |
| WO | 2008074033 A1 | 6/2008 |
| WO | 2008079404 A2 | 7/2008 |
| WO | 2008089008 A2 | 7/2008 |
| WO | 2008098960 A1 | 8/2008 |
| WO | 2008113056 A2 | 9/2008 |
| WO | 2008137474 A1 | 11/2008 |
| WO | 2009002297 A1 | 12/2008 |
| WO | 2009056791 A1 | 5/2009 |
| WO | 2009061934 A1 | 5/2009 |
| WO | 2010020969 A1 | 2/2010 |
| WO | WO2010073124 * | 7/2010 |
| WO | 2010115252 A1 | 10/2010 |
| WO | 2010127099 A2 | 11/2010 |
| WO | 2010147666 A1 | 12/2010 |
| WO | 2011017800 A1 | 2/2011 |
| WO | 2011060945 A2 | 5/2011 |
| WO | WO2011076708 * | 6/2011 |
| WO | 2011085211 A1 | 7/2011 |
| WO | 2011089216 A1 | 7/2011 |
| WO | 2011106688 A1 | 9/2011 |
| WO | 2011154833 A1 | 12/2011 |
| WO | 2012007352 A1 | 1/2012 |

(56) References Cited

FOREIGN PATENT DOCUMENTS

| | | |
|---|---|---|
| WO | 2012025213 A2 | 3/2012 |
| WO | 2012027543 A1 | 3/2012 |
| WO | 2012055567 A2 | 5/2012 |
| WO | 2012115695 A1 | 8/2012 |
| WO | 2013008182 A1 | 1/2013 |
| WO | 2013017974 A1 | 2/2013 |
| WO | 2013024376 A1 | 2/2013 |
| WO | 2013027150 A1 | 2/2013 |
| WO | 2013152608 A1 | 10/2013 |
| WO | 2013167988 A1 | 11/2013 |
| WO | 2013167993 A1 | 11/2013 |
| WO | 2013167996 A1 | 11/2013 |
| WO | 2013168022 A1 | 11/2013 |

OTHER PUBLICATIONS

"Progress Application of Fumaric Acid and the Derivatives of Fumaric Acid,Guangdong Chemical Industry", Guangdong Chemical Industry, Jul. 31, 2007, by Gao Cuiying1 et al. (p. 1) http://en.cnki.com.cn/Article_en/CJFDTOTAL-GDHG200707027.htm.

"1H and 13C Nuclear Magnetic Resonance Studies on the Tautomerism, Geometrical Isomerism and Conformation of some Cyclic Amidines, Guanidines and Related Systems", Journal of American Chemical Society, May 1975, by Lloyd M. Jackman et al. (p. 1) http://pubs.acs.org/doi/pdf/10.1021/ja00843a033.

"Enzyme-catalyzed regioselective synthesis of lipophilic guaifenesin ester derivatives", Journal of Molecular Catalysis B: Enzymatic, Feb. 2, 2004, by Na Wang et al. (p. 1) http://www.sciencedirect.com/science/article/pii/S1381117703002650.

"Interactions of the advanced glycation end product inhibitor pyridoxamine and the antioxidant α-lipoic acid on insulin resistance in the obese Zucker rat", Metabolism, Oct. 10, 2008 by Elizabeth A. Muellenbach et al. (p. 1) http://www.sciencedirect.com/science/article/pii/S0026049508002047.

"Effect of pentoxifylline and/or alpha lipoic acid on experimentally induced acute pancreatitis.", European Journal of Pharmacology, Jun. 21, 2010 by Amany A. Abdin et al. (p. 1) http://www.ncbi.nlm.nih.gov/pubmed/20599924.

"Pretreatment with pentoxifylline and N-acetylcysteine in liver ischemia reperfusion-induced renal injury.", Renal Failure, Feb. 27, 2012, by Behjat Seifi et al. (p. 1) http://www.ncbi.nlm.nih.gov/pubmed/22364443.

Synthesis and evaluation of Ketorolac ester prodrugs for transdermal delivery,Journal of Pharmaceutical Science, by Hea-Jeong Doh et al. May 2003 (p. 1) http://onlinelibrary.wiley.com/doi/10.1002/jps.10353/abstract.

Probing the skin permeation of fish oil EPA and ketoprofen 1. NMR spectroscopy and molecular modelling, International Journal of Pharmaceutics, by Christopher P. Thomas et al. Feb. 12, 2007 (pp. 2) http://www.sciencedirect.com/science/article/pii/S0378517307001330.

RN 67195-24-8 REGISTRY Entered STN: Nov. 16, 1984 (pp. 2) http://chem.sis.nlm.nih.gov/chemidplus/rn/67195-24-8.

"Palladium-Catalyzed Direct Arylation of Benzoxazoles with Unactivated Simple Arenes", Chemical Communications journal, Sep. 14, 2012, by Ge Wu et al. (pp. 84) http://www.rsc.org/suppdata/cc/c2/c2cc34238c/c2cc34238c.pdf.

"Tafamidis", from Nature Review Drug Discovery 11, Mar. 2012 by Gerard Said et al. (pp. 2) http://www.nature.com/nrd/journal/v11/n3/full/nrd3675.html.

"The role of structural information in the discovery of direct thrombin and factor Xa inhibitors", Trends in Pharmacological Sciences, vol. 33, Issue 5, Apr. 2012 (p. 1) http://www.cell.com/trends/pharmacological-sciences/abstract/S0165-6147(12)00036-3.

"Nicotinamide-substituted complexes as redox markers. 1. Synthesis and UV investigation of rhenium and technetium mixed-ligand systems", Journal of Labelled Compounds, Jan. 1998 by T. Kniess et al. (p. 1) http://www.researchgate.net/publication/243806712_Nicotinamide-substituted_complexes_as_redox_markers._1._Synthesis_and_UV_investigation_of_rhenium_and_technetium_mixed-ligand_systems.

\* cited by examiner

COMPOSITIONS AND METHODS FOR THE TREATMENT OF NEUROLOGIC DISEASES

PRIORITY

The present application claims the benefit of Indian Provisional Patent Application No. 1862/CHE/2012 filed on 10 May 2012 and the International Application No. PCT/IB2013/053122 filed on 19 Apr. 2013, the entire disclosure of which is relied on for all purposes and is incorporated into this application by reference.

FIELD OF THE INVENTION

This disclosure generally relates to compounds and compositions for the treatment of neurologic diseases. More particularly, this invention relates to treating subjects with a pharmaceutically acceptable dose of compounds, crystals, solvates, enantiomer or stereoisomer, esters, salts, hydrates, prodrugs, or mixtures thereof.

BACKGROUND OF THE INVENTION

Diseases of the central nervous system remain among the most compelling maladies known to humankind. This is because neurological disorders are typically devastating to affected patients and their families, often robbing individuals of the qualities that we most strongly associate with being human, and because the vast majority of neurological and neurodegenerative disorders lack effective therapies. In the 1980s and 1990s, the advent of molecular genetics approaches to map and identify disease genes laid the foundation for a prodigious advance in our understanding of the pathogenic basis of numerous important neurological disorders.

Neuropathic pain (NP) is a complex condition that has been the subject of considerable basic and clinical research. As a result of this effort, considerable progress has been made in our understanding of the pathophysiology underlying NP. Mechanisms now thought to be involved in the development and maintenance of NP include alterations in peripheral nerves, dorsal root ganglia, and the spinal cord. These changes include upregulation and/or downregulation of neuropeptides and neurotransmitters and changes that occur at supraspinal sites and result in facilitation of pain transmission.

Restless leg syndrome (RLS) is a disorder in which there is an urge or need to move the legs to move the legs to stop unpleasant sensations. RLS occurs most often in middle-aged and older adults. Stress makes it worse. The cause is not known in patients. RLS often occurs in patients with chronic kidney disease, diabetes, iron deficiency, parkinson's disease, peripheral neuropathy, pregnancy or with any other chronic diseases.

Neurodegenerative disorders are a heterogeneous group of diseases of the nervous system, including the brain, spinal cord, and peripheral nerves, that have many different aetiologies. Many are hereditary, some are secondary to toxic or metabolic processes, and others result from infections. Due to the prevalence, morbidity, and mortality of the neurodegenerative diseases, they represent significant medical, social, and financial burden on the society. Neuropathologically, these are characterised by abnormalities of relatively specific regions of the brain and specific populations of neurons. The degenerating neuron clusters in the different diseases determine the clinical phenotype of that particular illness.

Free radicals are highly reactive moieties playing an important role in health and disease. The central nervous system is especially vulnerable to free radical damage because of brain's high oxygen consumption, abundant lipid content and relative paucity of antioxidant enzymes compared with other tissues. Oxidative stress mediated cell damage in the pathophysiology of several CNS disorders has also been suggested. In view of the above, the present study was designed to investigate the effect of stress on neurobehavioral changes and the possible involvement of free radicals. Restraint stress (RS) was used as an experimental stressor and elevated plus maze was used as a test for anxiety.

Managing acute pathology of often relies on the addressing underlying pathology and symptoms of the disease. There is currently a need in the art for new compositions to treatment or delay of the onset of neurologic diseases and its associated complications progression.

SUMMARY OF THE INVENTION

The present invention provides compounds, compositions containing these compounds and methods for using the same to treat, prevent and/or ameliorate the effects of the conditions such as neurologic diseases.

The invention herein provides compositions comprising of formula I or pharmaceutical acceptable salts thereof. The invention also provides pharmaceutical compositions comprising one or more compounds of formula I or intermediates thereof and one or more of pharmaceutically acceptable carriers, vehicles or diluents. These compositions may be used in the treatment of neurologic diseases and its associated complications.

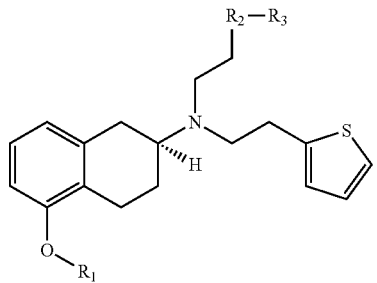

Formula I

In certain embodiments, the present invention relates to the compounds and compositions of formula I, or pharmaceutically acceptable salts thereof,

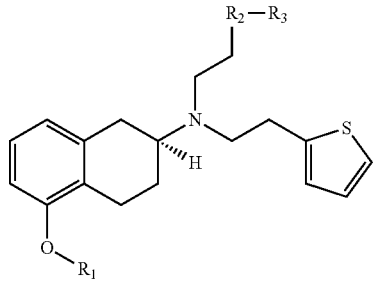

Formula I

Wherein,
$R^1$ represents —OH, —$CH_3$, —F, -D, —OD, —$NH_2$, —H, $CD_3CO$—, Acetyl, —Cl,

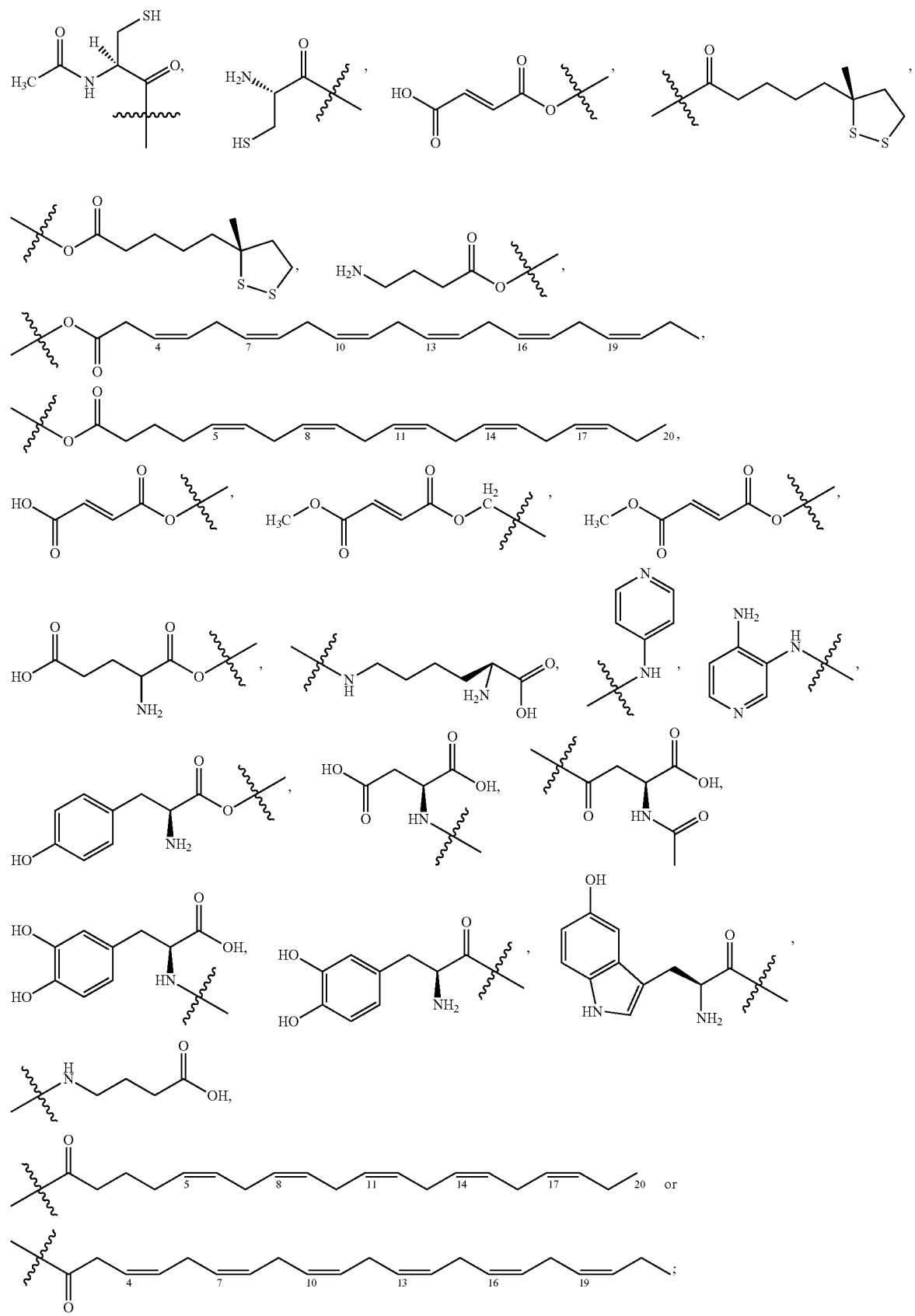

$R^2$ represents —CH$_3$CO—, acetyl, D, H, CH$_3$CO—, acetyl, D, H,
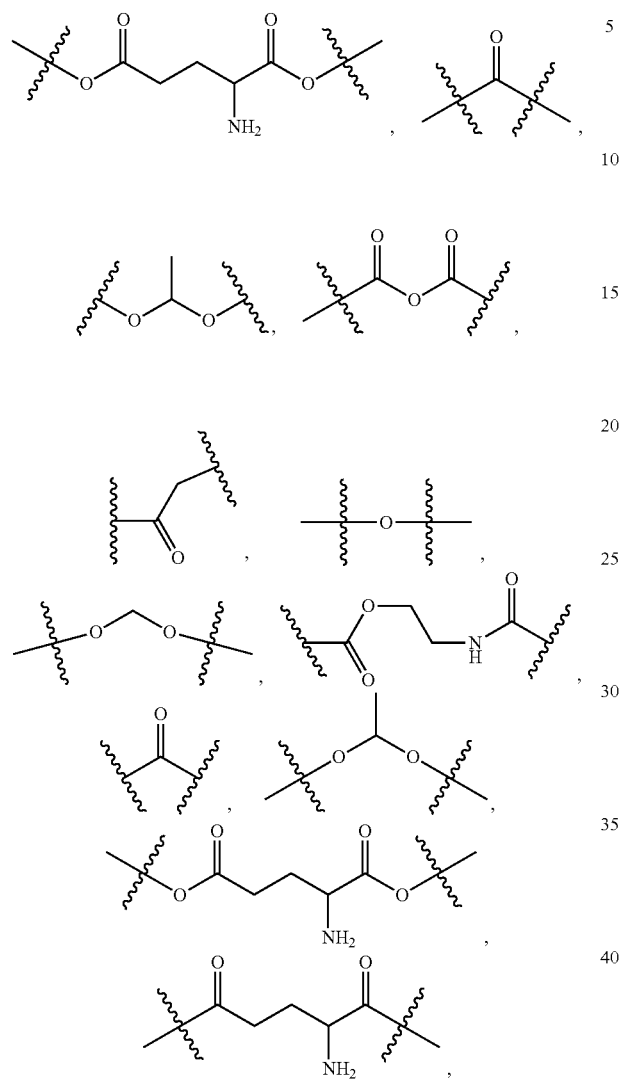
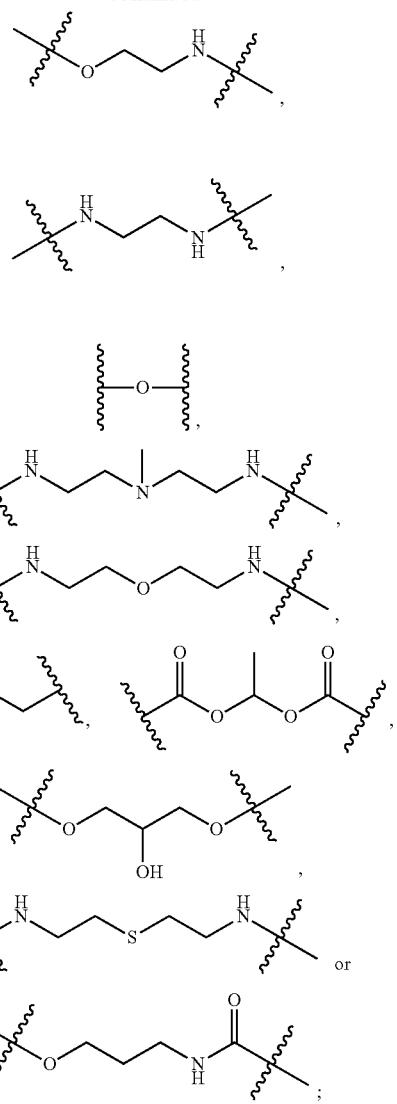
$R^3$ independently represents
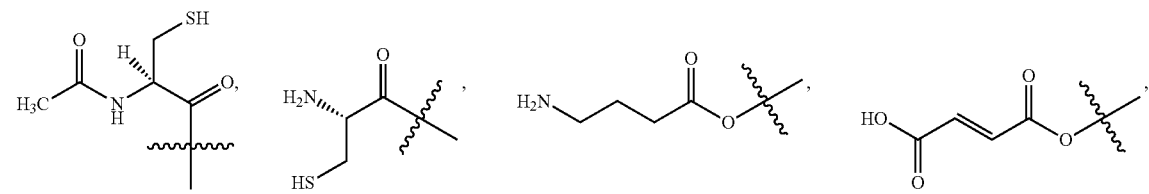
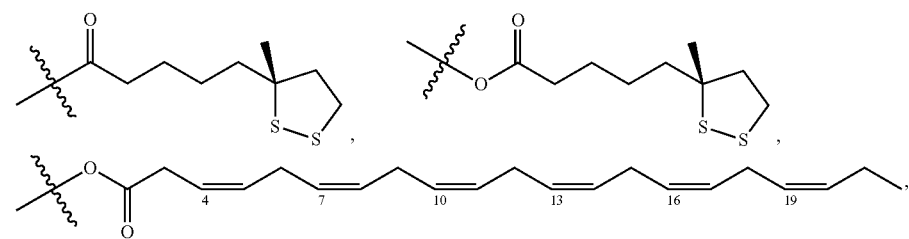

-continued
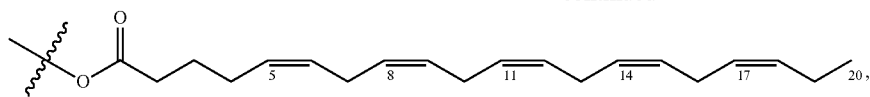
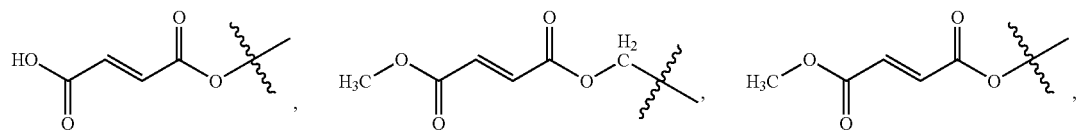
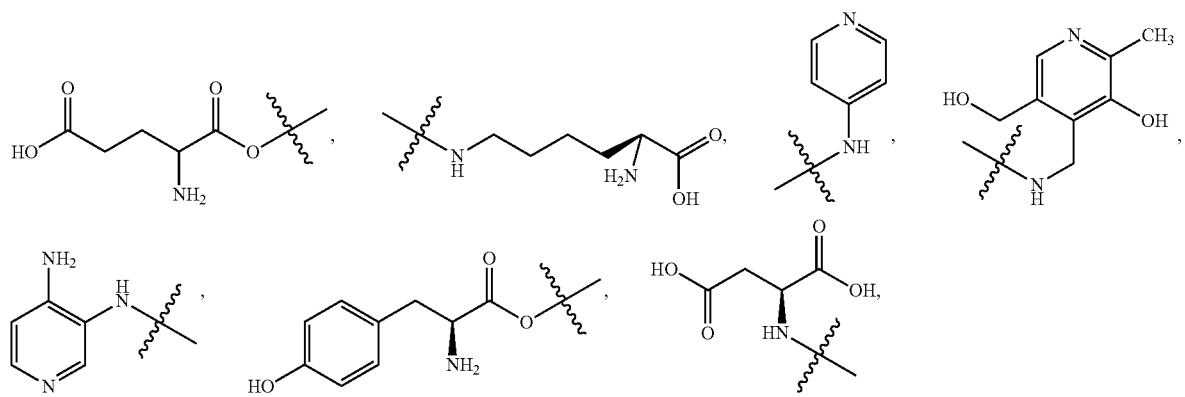
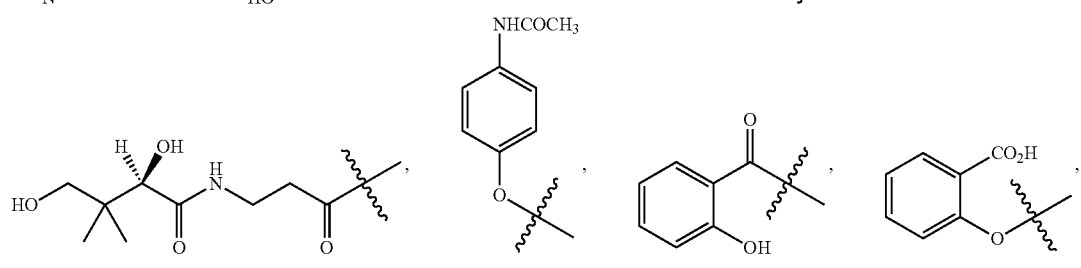
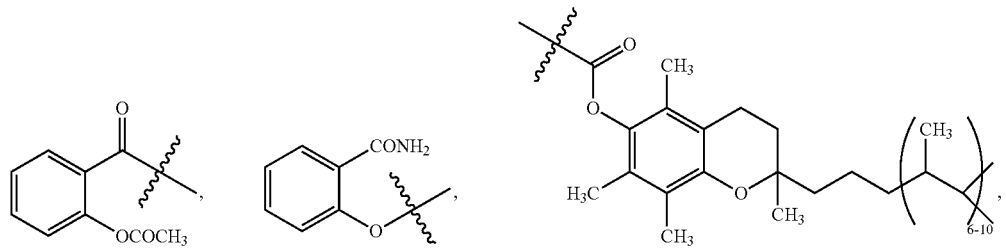
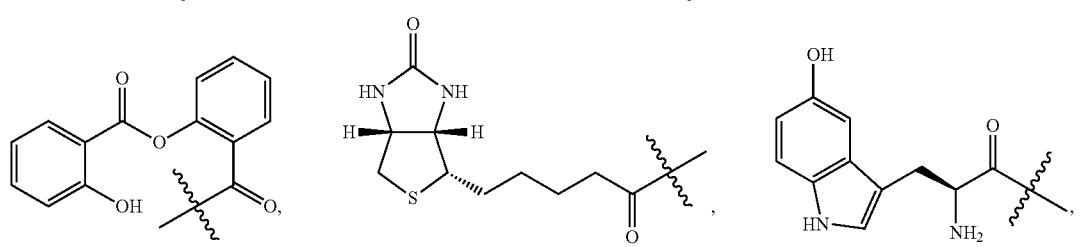
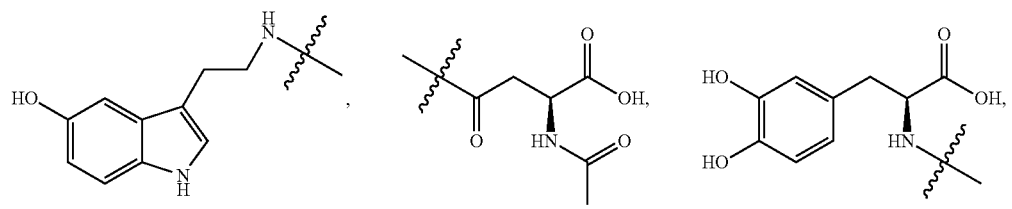

-continued

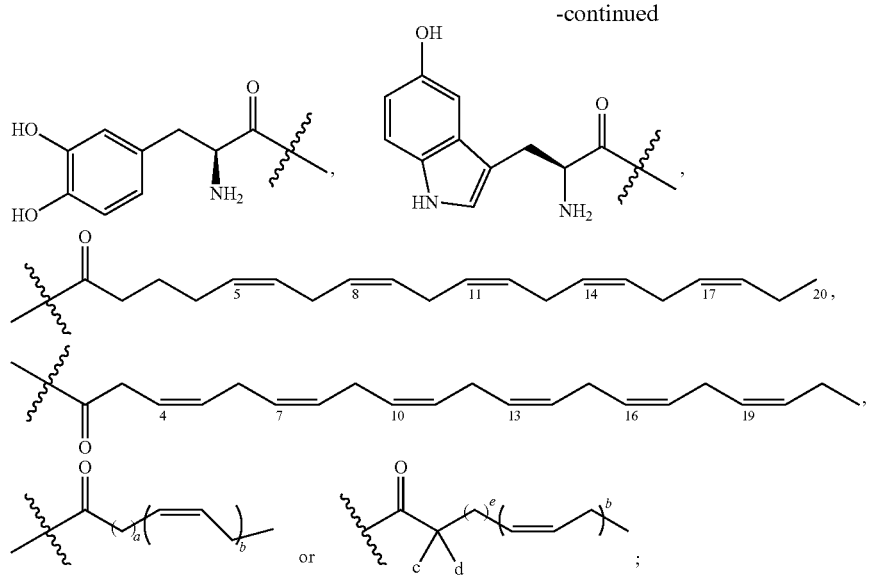

a is independently 2, 3 or 7;
each b is independently 3, 5 or 6;
is independently 1, 2 or 6;
c and d are each independently H, D, —OH, —OD, $C_1$-$C_6$-alkyl, —$NH_2$ or —$COCH_3$.

In the illustrative embodiments, examples of compounds of formula I are as set forth below:

maceutical composition is formulated for systemic administration, oral administration, sustained release, parenteral administration, injection, subdermal administration, or transdermal administration.

Herein, the application additionally provides kits comprising the pharmaceutical compositions described herein.

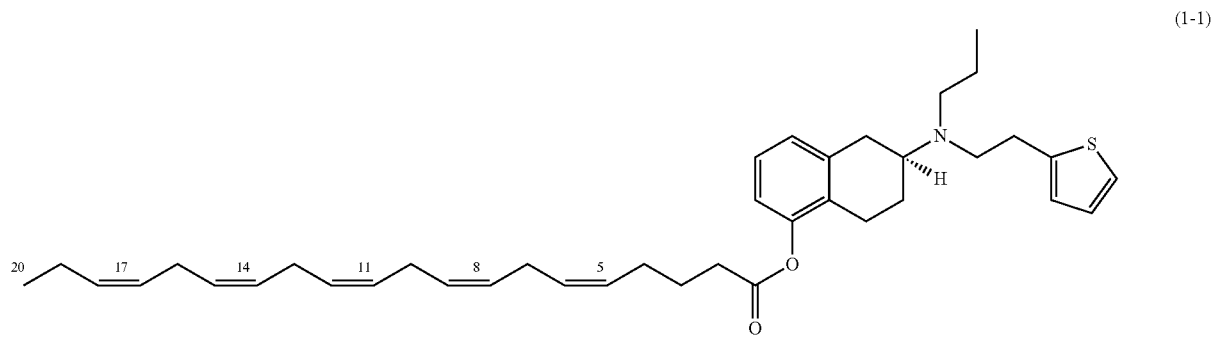

(1-1)

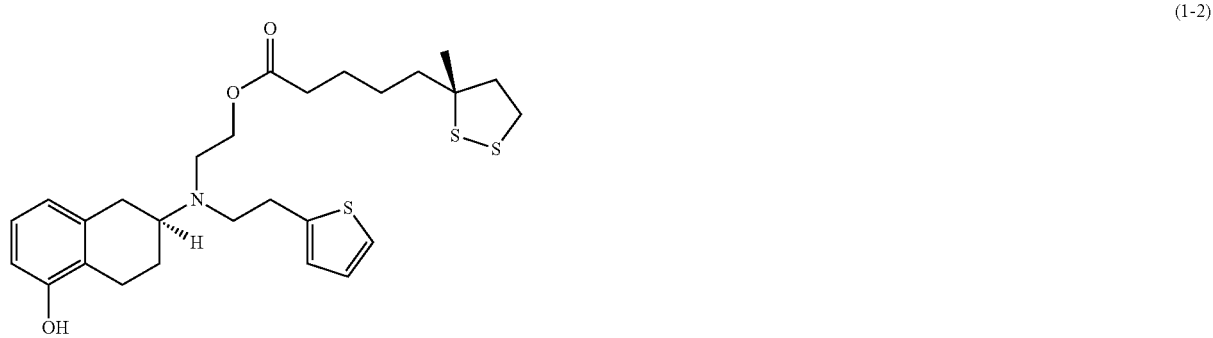

(1-2)

Herein the application also provides a kit comprising any of the pharmaceutical compositions disclosed herein. The kit may comprise instructions for use in the treatment of neurologic diseases or its related complications.

The application also discloses a pharmaceutical composition comprising a pharmaceutically acceptable carrier and any of the compositions herein. In some aspects, the phar- The kits may further comprise instructions for use in the treatment of neurologic diseases or its related complications.

The compositions described herein have several uses. The present application provides, for example, methods of treating a patient suffering from neurologic diseases or its related complications manifested from metabolic or genetic conditions or disorders, neurologic diseases, chronic diseases or disorders; neurodegenerative disorders, Hepatology, Cancer, Respiratory, Hematological, Orthopedic, Cardiovascular, Renal, Skin, Vascular or Ocular complications.

DETAILED DESCRIPTION OF THE INVENTION

Definitions

As used herein, the following terms and phrases shall have the meanings set forth below. Unless defined otherwise, all technical and scientific terms used herein have the same meaning as commonly understood to one of ordinary skill in the art.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be affected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "metabolic condition" refers to an Inborn errors of metabolism (or genetic metabolic conditions) are genetic disorders that result from a defect in one or more metabolic pathways; specifically, the function of an enzyme is affected and is either deficient or completely absent.

In some embodiments, a molecular conjugate comprises of compounds selected from the group consisting of R-lipoic acid (CAS No. 1200-22-2), salsalate (CAS No. 552-94-3), acetylcysteine (CAS No. 616-91-1), Eicosapentaenoic acid (CAS No. 10417-94-4), Docosahexaenoic acid (CAS No. 6217-54-5).

The term "polymorph" as used herein is art-recognized and refers to one crystal structure of a given compound.

The phrases "parenteral administration" and "administered parenterally" as used herein refer to modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "predicting" as used herein refers to assessing the probability related diseases patient will suffer from abnormalities or complication and/or terminal platelet aggregation or failure and/or death (i.e. mortality) within a defined time window (predictive window) in the future. The mortality may be caused by the central nervous system or complication. The predictive window is an interval in which the subject will develop one or more of the said complications according to the predicted probability. The predictive window may be the entire remaining lifespan of the subject upon analysis by the method of the present invention.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the epilepsy, migraine, depression, restless leg syndrome, Creutzfeld-Jakob disease, Alzheimer's disease, multiple sclerosis, Batten disease, multiple sclerosis, Parkinson's disease (PD), restless legs syndrome (RLS), cluster headache, depression, fibromyalgia, sexual dysfunction, amyotrophic lateral sclerosis (ALS), also known as Lou Gehrig's disease, convulsions, partial seizures, or as an adjunctive therapy for partial, myoclonic, tonic-clonic seizures, mood-stabilizing agent, bipolar disorder, Tourette syndrome, Alzheimer's disease, autism, bipolar disorder and anxiety disorder, trigeminal neuralgia, attention-deficit hyperactivity disorder, schizophrenia, neuropathic pain, seizures, bipolar disorder, mania, phantom limb syndrome, complex regional pain syndrome, paroxysmal extreme pain disorder, neuromyotonia, intermittent explosive disorder, borderline personality disorder, myotonia congenita and post-traumatic stress disorder of a subject by administration of an agent even though such agent does not treat the cause of the condition. The term "treating", "treat" or "treatment" as used herein includes curative, preventative (e.g., prophylactic), adjunct and palliative treatment.

The phrase "therapeutically effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

In certain embodiments, the pharmaceutical compositions described herein are formulated in a manner such that said compositions will be delivered to a patient in a therapeutically effective amount, as part of a prophylactic or therapeutic treatment. The desired amount of the composition to be administered to a patient will depend on absorption, inactivation, and excretion rates of the drug as well as the delivery rate of the salts and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular salt or composition may be adjusted to accommodate variations in the treatment parameters. Such treatment parameters include the clinical use to which the preparation is put, e.g., the site treated, the type of patient, e.g., human or non-human, adult or child, and the nature of the disease or condition.

In certain embodiments, the dosage of the subject compositions provided herein may be determined by reference to the plasma concentrations of the therapeutic composition or other encapsulated materials. For example, the maximum plasma concentration (Cmax) and the area under the plasma concentration-time curve from time 0 to infinity may be used.

When used with respect to a pharmaceutical composition or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active salt and/or composition, for a sustained or extended period (as compared to the release from a bolus). This release may result in prolonged delivery of therapeutically effective amounts of any of the therapeutic agents disclosed herein.

The phrases "systemic administration," "administered systemically," "peripheral administration" and "administered peripherally" are art-recognized, and include the administration of a subject composition, therapeutic or other material at a site remote from the disease being treated. Administration of an agent for the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The present disclosure also contemplates prodrugs of the compositions disclosed herein, as well as pharmaceutically acceptable salts of said prodrugs.

This application also discloses a pharmaceutical composition comprising a pharmaceutically acceptable carrier and the composition of a compound of Formula I may be formulated for systemic or topical or oral administration. The pharmaceutical composition may be also formulated for oral administration, oral solution, injection, subdermal administration, or transdermal administration. The pharmaceutical composition may further comprise at least one of a pharmaceutically acceptable stabilizer, diluent, surfactant, filler, binder, and lubricant.

In many embodiments, the pharmaceutical compositions described herein will incorporate the disclosed compounds and compositions (Formula I) to be delivered in an amount sufficient to deliver to a patient a therapeutically effective amount of a compound of formula I or composition as part of a prophylactic or therapeutic treatment. The desired concentration of formula I or its pharmaceutical acceptable salts will depend on absorption, inactivation, and excretion rates of the drug as well as the delivery rate of the salts and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular compound of formula I may be adjusted to accommodate variations in the treatment parameters. Such treatment parameters include the clinical use to which the preparation is put, e.g., the site treated, the type of patient, e.g., human or non-human, adult or child, and the nature of the disease or condition.

The concentration and/or amount of any compound of formula I may be readily identified by routine screening in animals, e.g., rats, by screening a range of concentration and/or amounts of the material in question using appropriate assays. Known methods are also available to assay local tissue concentrations, diffusion rates of the salts or compositions, and local blood flow before and after administration of therapeutic formulations disclosed herein. One such method is microdialysis, as reviewed by T. E. Robinson et al., 1991, microdialysis in the neurosciences, Techniques, volume 7, Chapter 1. The methods reviewed by Robinson may be applied, in brief, as follows. A microdialysis loop is placed in situ in a test animal. Dialysis fluid is pumped through the loop. When compounds with formula I such as those disclosed herein are injected adjacent to the loop, released drugs are collected in the dialysate in proportion to their local tissue concentrations. The progress of diffusion of the salts or compositions may be determined thereby with suitable calibration procedures using known concentrations of salts or compositions.

In certain embodiments, the dosage of the subject compounds of formula I provided herein may be determined by reference to the plasma concentrations of the therapeutic composition or other encapsulated materials. For example, the maximum plasma concentration (Cmax) and the area under the plasma concentration-time curve from time 0 to infinity may be used.

Generally, in carrying out the methods detailed in this application, an effective dosage for the compounds of Formulas I is in the range of about 0.01 mg/kg/day to about 100 mg/kg/day in single or divided doses, for instance 0.01 mg/kg/day to about 50 mg/kg/day in single or divided doses. The compounds of Formulas I may be administered at a dose of, for example, less than 0.2 mg/kg/day, 0.5 mg/kg/day, 1.0 mg/kg/day, 5 mg/kg/day, 10 mg/kg/day, 20 mg/kg/day, 30 mg/kg/day, or 40 mg/kg/day. Compounds of Formula I may also be administered to a human patient at a dose of, for example, between 0.1 mg and 1000 mg, between 5 mg and 80 mg, or less than 1.0, 9.0, 12.0, 20.0, 50.0, 75.0, 100, 300, 400, 500, 800, 1000, 2000, 5000 mg per day. In certain embodiments, the compositions herein are administered at an amount that is less than 95%, 90%, 80%, 70%, 60%, 50%, 40%, 30%, 20%, or 10% of the compound of formula I required for the same therapeutic benefit.

An effective amount of the compounds of formula I described herein refers to the amount of one of said salts or compositions which is capable of inhibiting or preventing a disease.

An effective amount may be sufficient to prohibit, treat, alleviate, ameliorate, halt, restrain, slow or reverse the progression, or reduce the severity of a complication resulting from nerve damage or demyelization and/or elevated reactive oxidative-nitrosative species and/or abnormalities in physiological homeostasis's, in patients who are at risk for such complications. As such, these methods include both medical therapeutic (acute) and/or prophylactic (prevention) administration as appropriate. The amount and timing of compositions administered will, of course, be dependent on the subject being treated, on the severity of the affliction, on the manner of administration and on the judgment of the prescribing physician. Thus, because of patient-to-patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

The compositions provided by this application may be administered to a subject in need of treatment by a variety of conventional routes of administration, including orally, topically, parenterally, e.g., intravenously, subcutaneously or intramedullary. Further, the compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

The compositions may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compositions and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as L-arginine, sodium citrate, calcium carbonate and calcium phosphate may be employed along with various disintegrates such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Appropriate materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof. The compounds of formula I may also comprise enterically coated comprising of various excipients, as is well known in the pharmaceutical art.

For parenteral administration, solutions of the compositions may be prepared in (for example) sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The formulations, for instance tablets, may contain e.g. 10 to 100, 50 to 250, 150 to 500 mg, or 350 to 800 mg e.g. 10, 50, 100, 300, 500, 700, 800 mg of the compounds of formula I disclosed herein, for instance, compounds of formula I or pharmaceutical acceptable salts of a compounds of Formula I.

Generally, a composition as described herein may be administered orally, or parenterally (e.g., intravenous, intramuscular, subcutaneous or intramedullary). Topical administration may also be indicated, for example, where the patient is suffering from gastrointestinal disorder that prevent oral administration, or whenever the medication is best applied to the surface of a tissue or organ as determined by the attending physician. Localized administration may also be indicated, for example, when a high dose is desired at the target tissue or organ. For buccal administration the active composition may take the form of tablets or lozenges formulated in a conventional manner.

The dosage administered will be dependent upon the identity of the metabolic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. For oral administration either solid or fluid unit dosage forms can be prepared.

As discussed above, the tablet core contains one or more hydrophilic polymers. Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, high-molecular weight crosslinked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

The carrier may contain one or more suitable excipients for the formulation of tablets. Examples of suitable excipients include, but are not limited to, fillers, adsorbents, binders, disintegrants, lubricants, glidants, release-modifying excipients, superdisintegrants, antioxidants, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the tablet core contains up to about 5 percent by weight of such super disintegrant.

Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid, and mixtures thereof.

In one embodiment, the immediate release coating has an average thickness of at least 50 microns, such as from about 50 microns to about 2500 microns; e.g., from about 250 microns to about 1000 microns. In embodiment, the immediate release coating is typically compressed at a density of more than about 0.9 g/cc, as measured by the weight and volume of that specific layer.

In one embodiment, the immediate release coating contains a first portion and a second portion, wherein at least one of the portions contains the second pharmaceutically active agent. In one embodiment, the portions contact each other at a center axis of the tablet. In one embodiment, the first portion includes the first pharmaceutically active agent and the second portion includes the second pharmaceutically active agent.

In one embodiment, the first portion contains the first pharmaceutically active agent and the second portion contains the second pharmaceutically active agent. In one embodiment, one of the portions contains a third pharmaceutically active agent. In one embodiment one of the portions contains a second immediate release portion of the same pharmaceutically active agent as that contained in the tablet core.

In one embodiment, the outer coating portion is prepared as a dry blend of materials prior to addition to the coated tablet core. In another embodiment the outer coating portion is included of a dried granulation including the pharmaceutically active agent.

Formulations with different drug release mechanisms described above could be combined in a final dosage form containing single or multiple units. Examples of multiple units include multilayer tablets, capsules containing tablets, beads, or granules in a solid or liquid form. Typical, immediate release formulations include compressed tablets, gels, films, coatings, liquids and particles that can be encapsulated, for example, in a gelatin capsule. Many methods for preparing coatings, covering or incorporating drugs, are known in the art.

The immediate release dosage, unit of the dosage form, i.e., a tablet, a plurality of drug-containing beads, granules or particles, or an outer layer of a coated core dosage form, contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads).

Extended release formulations are generally prepared as diffusion or osmotic systems, for example, as described in "Remington—The Science and Practice of Pharmacy", 20th. Ed., Lippincott Williams & Wilkins, Baltimore, Md., 2000). A diffusion system typically consists of one of two types of devices, reservoir and matrix, which are wellknown and described in die art. The matrix devices are generally prepared by compressing the drug with a slowly dissolving polymer carrier into a tablet form.

An immediate release portion can be added to the extended release system by means of either applying an immediate release layer on top of the extended release core; using coating or compression processes or in a multiple unit system such as a capsule containing extended and immediate release beads.

Delayed release dosage formulations are created by coating a solid dosage form with a film of a polymer which is insoluble in the acid environment of the stomach, but soluble in the neutral environment of small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule.

A pulsed release dosage form is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

Each dosage form contains a therapeutically effective amount of active agent. In one embodiment of dosage forms that mimic a twice daily dosing profile, approximately 30 wt. % to 70 wt. %, preferably 40 wt. % to 60 wt. %, of the total amount of active agent in the dosage form is released in the initial pulse, and, correspondingly approximately 70 wt. % to 3.0 wt. %, preferably 60 wt. % to 40 wt. %, of the total amount of active agent in the dosage form is released in the second pulse. For dosage forms mimicking the twice daily dosing profile, the second pulse is preferably released approximately 3 hours to less than 14 hours, and more preferably approximately 5 hours to 12 hours, following administration.

Another dosage form contains a compressed tablet or a capsule having a drug-containing immediate release dosage unit, a delayed release dosage unit and an optional second delayed release dosage unit. In this dosage form, the immediate release dosage unit contains a plurality of beads, granules particles that release drug substantially immediately following oral administration to provide an initial dose. The delayed release dosage unit contains a plurality of coated beads or granules, which release drug approximately 3 hours to 14 hours following oral administration to provide a second dose.

For purposes of transdermal (e.g., topical) administration, dilute sterile, aqueous or partially aqueous solutions (usually in about 0.1% to 5% concentration), otherwise similar to the above parenteral solutions, may be prepared.

Methods of preparing various pharmaceutical compositions with a certain amount of one or more compounds of formula I or other active agents are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

Methods of preparing these formulations or compositions include the step of bringing into association subject compositions with the carrier and, optionally, one or more accessory ingredients. In general, the formulations are prepared by uniformly and intimately bringing into association a subject composition with liquid carriers, or finely divided solid carriers, or both, and then, if necessary, shaping the product.

The compounds of formula I described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the subject compositions, may contain suspending agents such as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

Methods of delivering a composition or compositions via a transdermal patch are known in the art. Exemplary patches and methods of patch delivery are described in U.S. Pat. Nos. 6,974,588, 6,564,093, 6,312,716, 6,440,454, 6,267,983, 6,239,180, and 6,103,275.

In another embodiment, a transdermal patch may comprise: a substrate sheet comprising a composite film formed of a resin composition comprising 100 parts by weight of a polyvinyl chloride-polyurethane composite and 2-10 parts by weight of a styrene-ethylene-butylene-styrene copolymer, a first adhesive layer on the one side of the composite film, and a polyalkylene terephthalate film adhered to the one side of the composite film by means of the first adhesive layer, a primer layer which comprises a saturated polyester resin and is formed on the surface of the polyalkylene terephthalate film; and a second adhesive layer comprising a styrene-diene-styrene block copolymer containing a pharmaceutical agent layered on the primer layer. A method for the manufacture of the above-mentioned substrate sheet comprises preparing the above resin composition molding the resin composition into a composite film by a calendar process, and then adhering a polyalkylene terephthalate film on one side of the composite film by means of an adhesive layer thereby forming the substrate sheet, and forming a primer layer comprising a saturated polyester resin on the outer surface of the polyalkylene terephthalate film.

Another type of patch comprises incorporating the drug directly in a pharmaceutically acceptable adhesive and laminating the drug-containing adhesive onto a suitable backing member, e.g. a polyester backing membrane. The drug should be present at a concentration which will not affect the adhesive properties, and at the same time deliver the required clinical dose.

Transdermal patches may be passive or active. Passive transdermal drug delivery systems currently available, such as the nicotine, estrogen and nitroglycerine patches, deliver small-molecule drugs. Many of the newly developed proteins and peptide drugs are too large to be delivered through passive transdermal patches and may be delivered using technology such as electrical assist (iontophoresis) for large-molecule drugs.

Iontophoresis is a technique employed for enhancing the flux of ionized substances through membranes by application of electric current. One example of an iontophoretic membrane is given in U.S. Pat. No. 5,080,646 to Theeuwes. The principal mechanisms by which iontophoresis enhances molecular transport across the skin are (a) repelling a charged ion from an electrode of the same charge, (b) electroosmosis, the convective movement of solvent that occurs through a charged pore in response the preferential passage of counter-ions when an electric field is applied or (c) increase skin permeability due to application of electrical current.

In some cases, it may be desirable to administer in the form of a kit, it may comprise a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are widely used for the packaging of pharmaceutical unit dosage forms (tablets, capsules, and the like). Blister packs generally consist of a sheet of relatively stiff material covered with a foil of a plastic material that may be transparent.

Methods and compositions for the treatment of neurologic diseases. Among other things, herein is provided a method of treating neurologic diseases, comprising administering to a patient in need thereof a therapeutically effective amount of compound of Formula I:

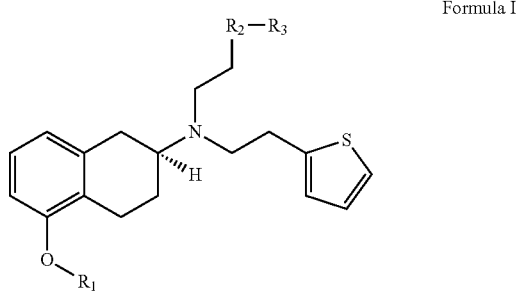

Formula I

Wherein,
$R^1$ represents —OH, —CH$_3$, —F, -D, —OD, —NH$_2$, —H, CD$_3$CO—, Acetyl, —Cl,

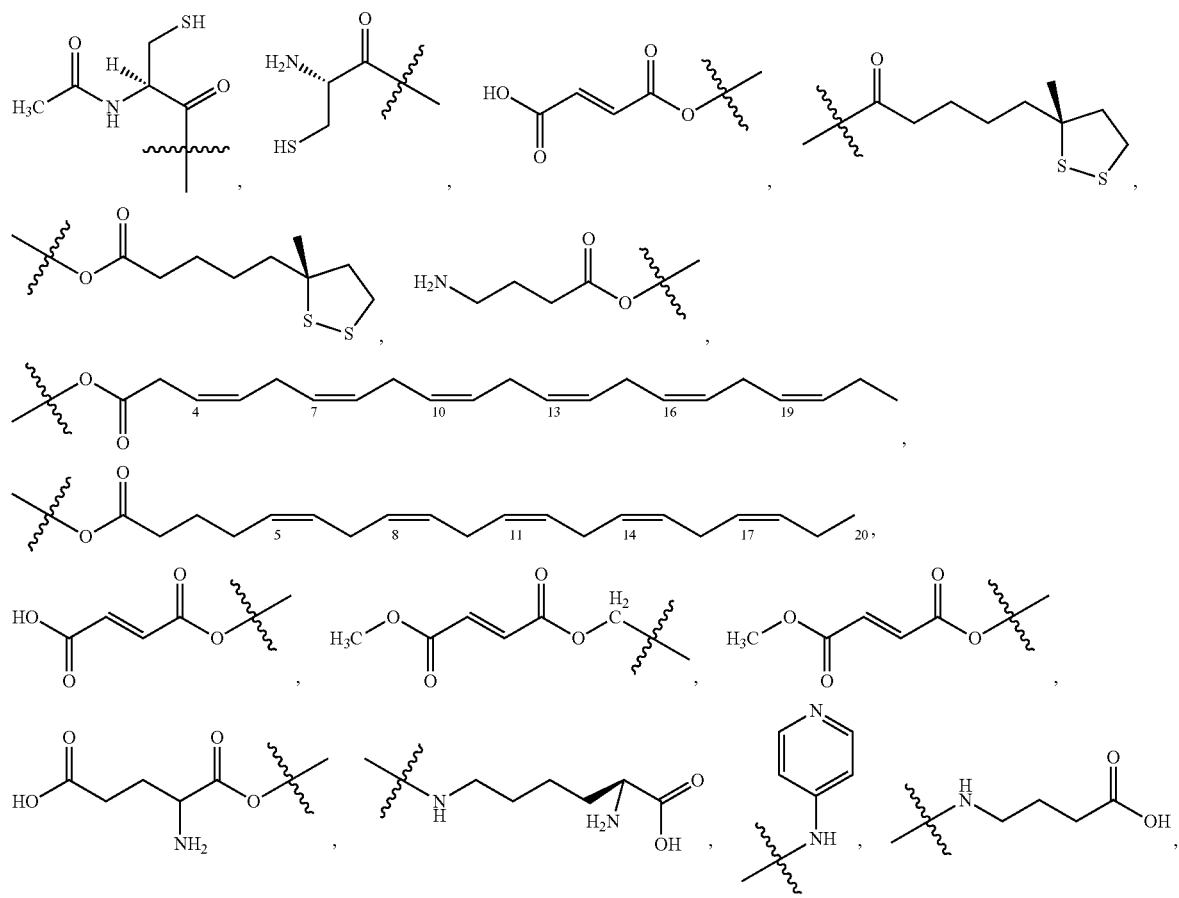

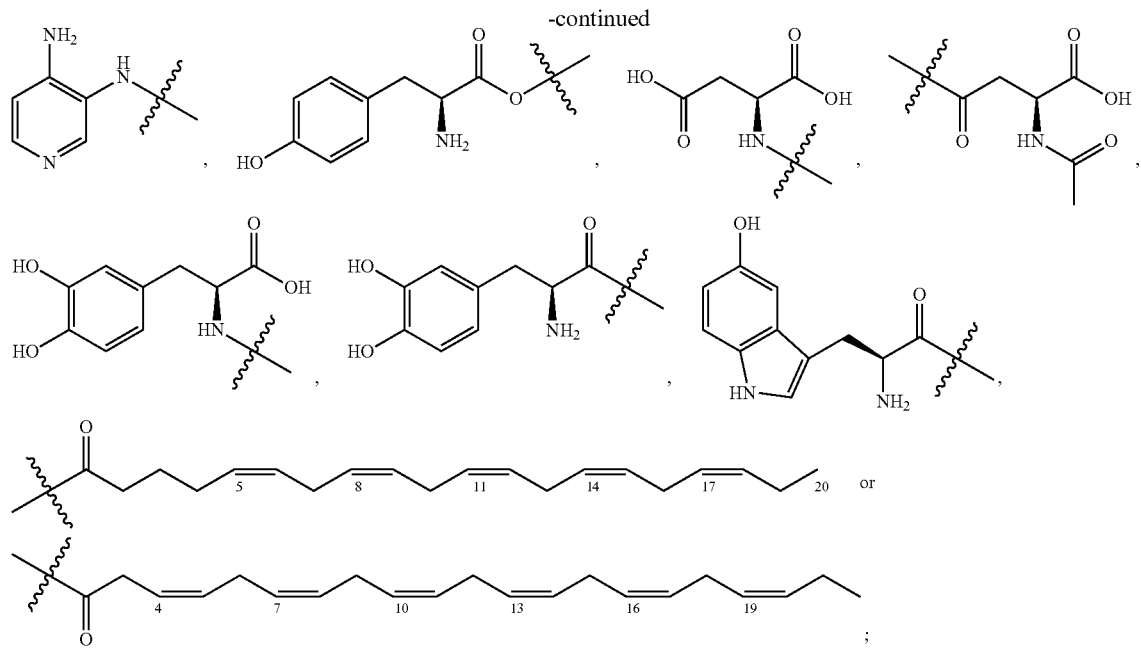
$R^2$ represents —CH$_3$CO—, acetyl, D, H, CH$_3$CO—, acetyl, D, H,
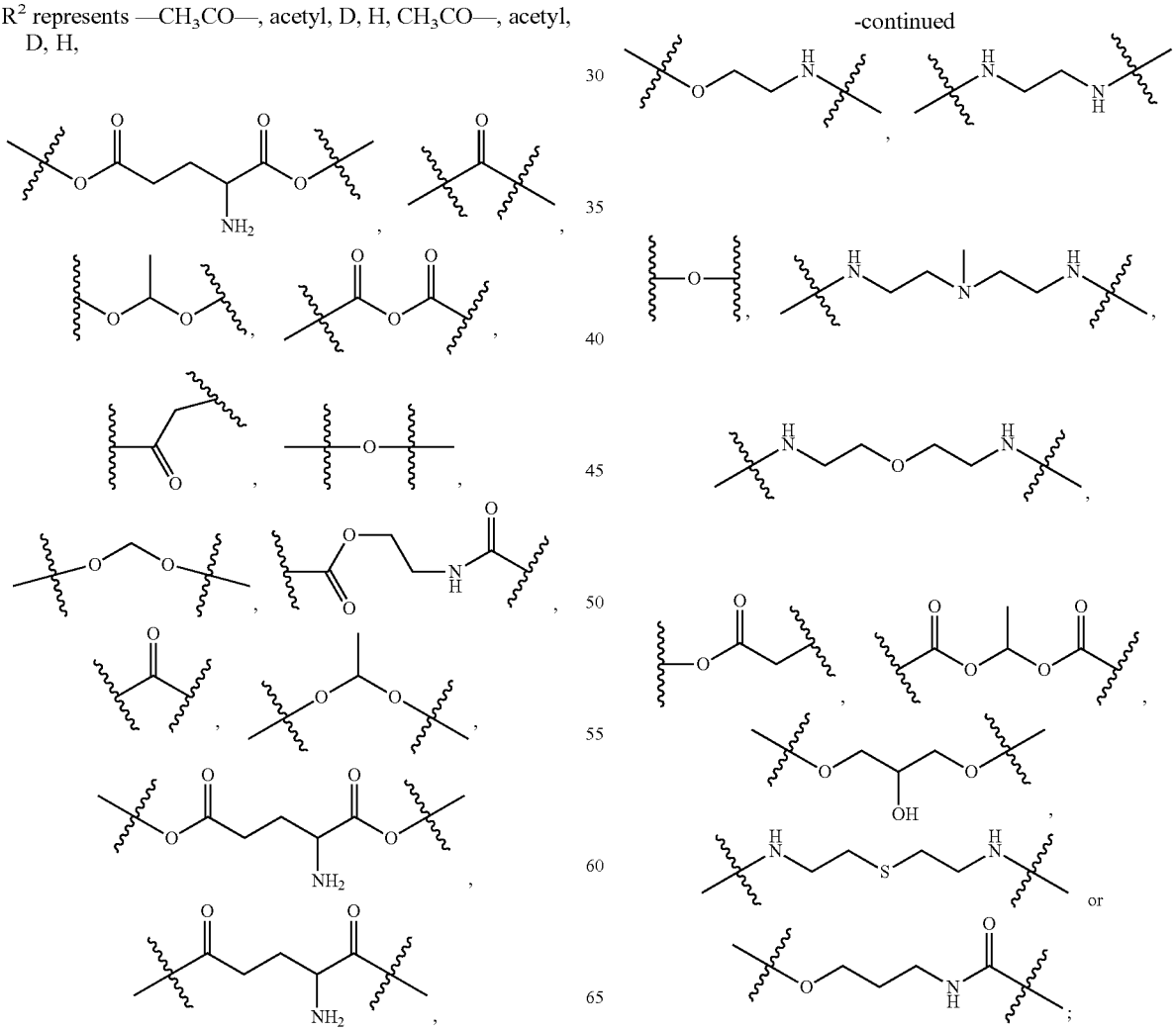

R³ represents
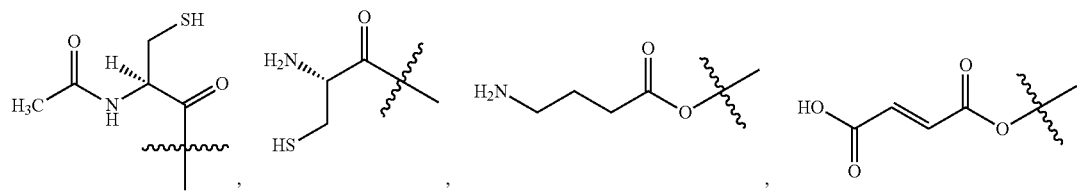
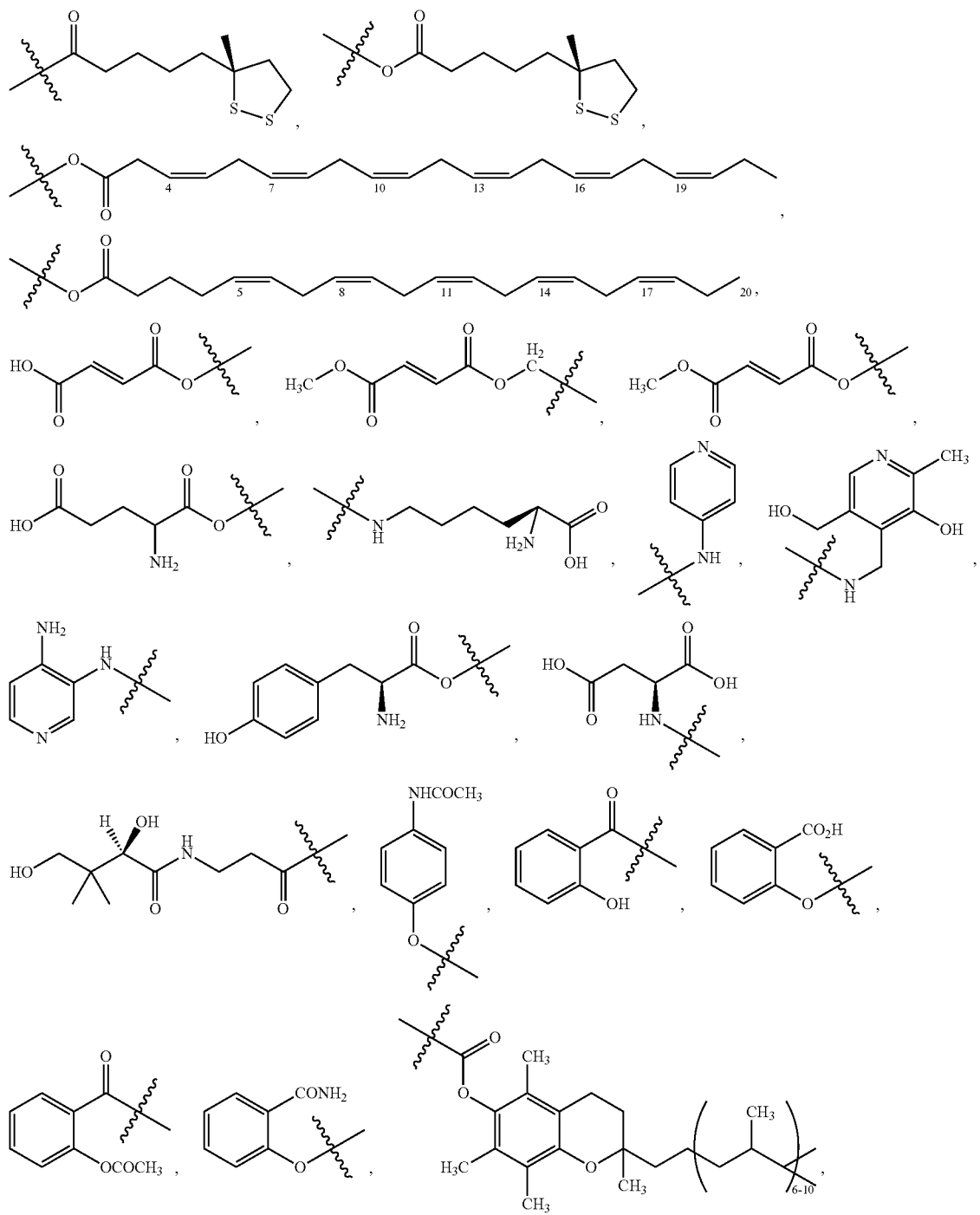

-continued

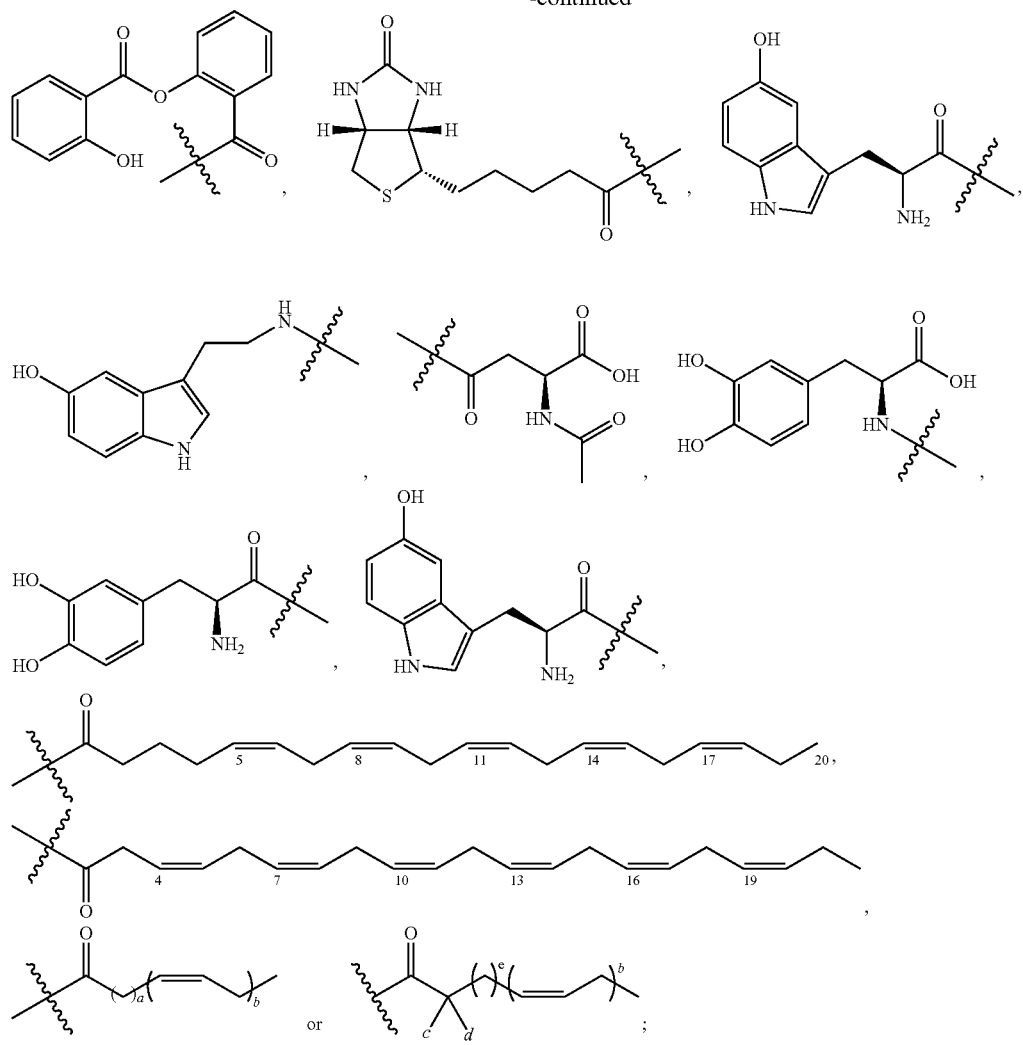

a is independently 2, 3 or 7;
each b is independently 3, 5 or 6;
e is independently 1, 2 or 6;
c and d are each independently H, D, —OH, —OD, $C_1$-$C_6$-alkyl, —$NH_2$ or —$COCH_3$.

Methods for Using Compounds of Formula I:

The invention also includes methods for treating epilepsy, migraine, depression, restless leg syndrome, Creutzfeld-Jakob disease, Alzheimer's disease, multiple sclerosis, Batten disease, multiple sclerosis, Parkinson's disease (PD), restless legs syndrome (RLS), cluster headache, depression, fibromyalgia, sexual dysfunction, amyotrophic lateral sclerosis (ALS), also known as Lou Gehrig's disease, convulsions, partial seizures, or as an adjunctive therapy for partial, myoclonic, tonic-clonic seizures, mood-stabilizing agent, bipolar disorder, Tourette syndrome, Alzheimer's disease, autism, bipolar disorder and anxiety disorder, trigeminal neuralgia, attention-deficit hyperactivity disorder, schizophrenia, neuropathic pain, seizures, bipolar disorder, mania, phantom limb syndrome, complex regional pain syndrome, paroxysmal extreme pain disorder, neuromyotonia, intermittent explosive disorder, borderline personality disorder, myotonia congenita and post-traumatic stress disorder.

Methods of Making

Examples of synthetic pathways useful for making compounds of formula I are set forth in example below and generalized in scheme 1:

Scheme-1:

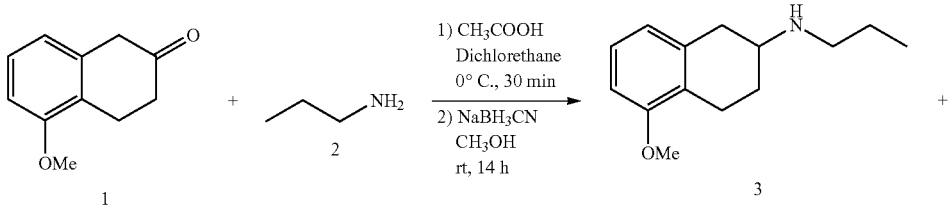

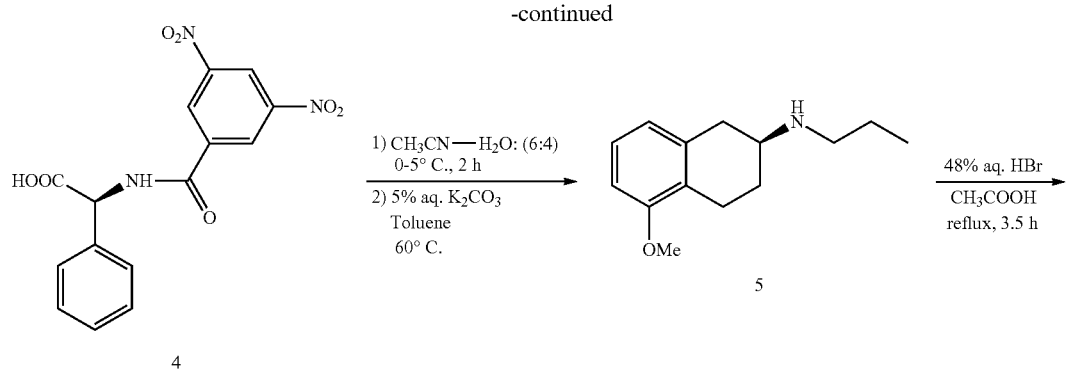
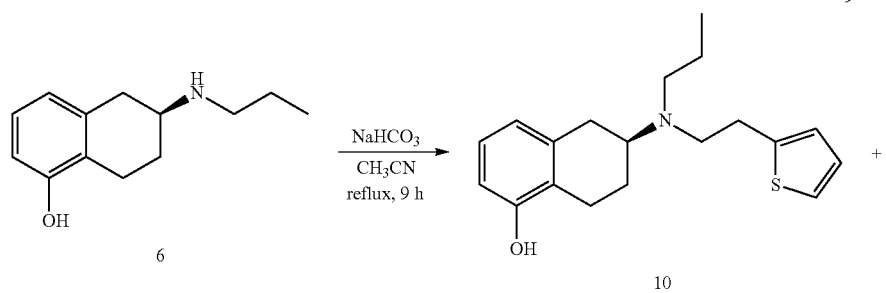
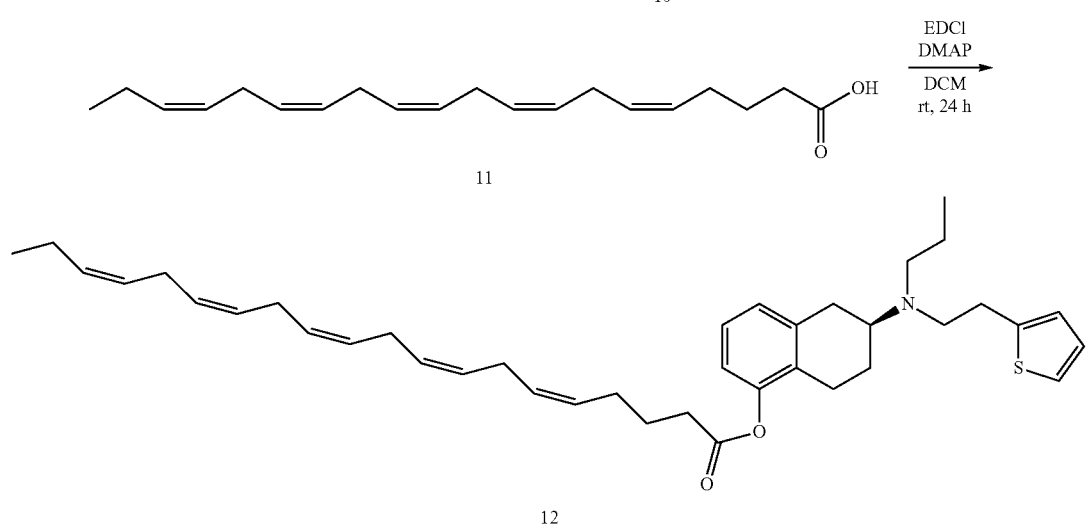

Step-1: Synthesis of Compound 2

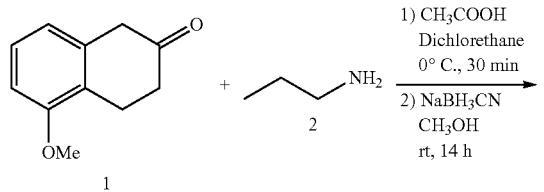

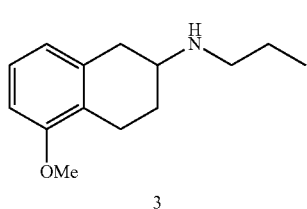

5-Methoxy-2-tetralone (10 g, 56.75 mmol) and acetic acid (13.5 ml, 226.9 mmol) were dissolved in dichloroethane (150 ml) and cooled to 0° C. n-propyl amine 2 (11.7 ml, 141.87 mmol) was added and the mixture stirred under a $N_2$ atmosphere for 30 min. $NaCNBH_3$ (8.915 g, 141.87 mmol) in anhydrous MeOH (15 ml) was then added to the mixture and allowed to stir overnight at ambient temperature. The volatiles were then evaporated and saturated $NaHCO_3$ solution was added. It was then extracted with dichloromethane, dried over $Na_2SO_4$, filtered, and concentrated. The crude residue was then taken up in EtOAc, at which time ethereal HCl was added, and the crude salt was filtered and dried over vacuum oven. The crude salt was then recrystalized in ethanol to yield 9.5 g (65%) white solid 3 and used in the subsequent transformations.

Step-2: Synthesis of Compound 5

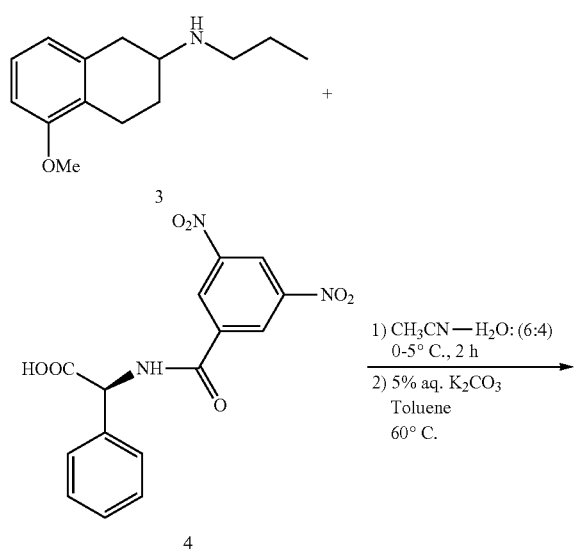

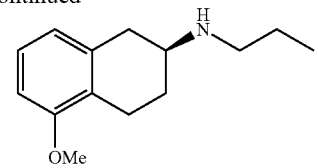

10 g of 3 were dissolved in 120 mL of an acetonitrile-water mixture (60:40). Then, 9.4 g (0.6 equivalents) of (+)-N-(3,5-dinitrobenzoyl)-α-phenylglycine 4 were added. The mixture was heated until dissolution. After the mixture was slowly cooled, turbidity appeared first and then a solid precipitate appeared. The mixture was left to stand at 0-5° C. for 2 hours. The suspension was filtered off and the resulting solid was oven dried.

9.8 g of the salt (38% yield) were obtained. The resultant product was analyzed by HPLC and showed an enantiomer ratio of 83:17. The solid was recrystallized successively in 10 volumes of an acetonitrile-water mixture (80:20), heated to reflux and then cooled to 0-5° C. After three recrystallizations, 3.8 g (15% overall yield) of salt were obtained which by chiral HPLC showed an (S)-enantiomer ratio higher than 99.5%. The purified dry salt was suspended under stirring in a mixture of toluene (20 mL) and 5% $K_2CO_3$ (60 mL) and heated to 60° C. until complete dissolution. The layers were separated and the organic layer was washed with 5% $K_2CO_3$ (15 mL), followed by water (8 mL). The organic layer was concentrated until the solvent was completely removed. 1.44 g of 5 was obtained as an oil (98%=yield).

Step-3: Synthesis of Compound 6

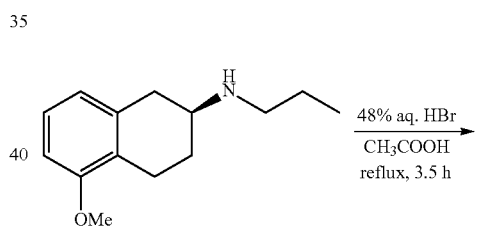

10 g of (S)-(−)-2-(N-propylamino)-5-methoxytetraline, 5 were mixed with 40 mL of 48% HBr and 20 mL of acetic acid. The resulting mixture was refluxed for 3 hours. During this time period, precipitation of a solid began. The suspension was gradually cooled to 0-5° C. and 30 mL of water were added. The reaction mixture was filtered off and 11.7 g (90% yield) of S-(−)-2-(N-propylamino)-5-hydroxytetraline bromhydrate were obtained. This solid was suspended in 110 mL of water and the suspension was heated to 40° C. 10M NaOH was added until the pH was 12.5, and the mixture became a solution. Later, the mixture was acidified to pH 9-9.5 with 6M HCl and precipitation of a solid occurred. The mixture was gradually cooled to 0-5° C. and filtered off. 7.5 g of S-(−−)-2-(N-propylamino)-5-hydroxytetraline 6.

Step-4: Synthesis of Compound 9

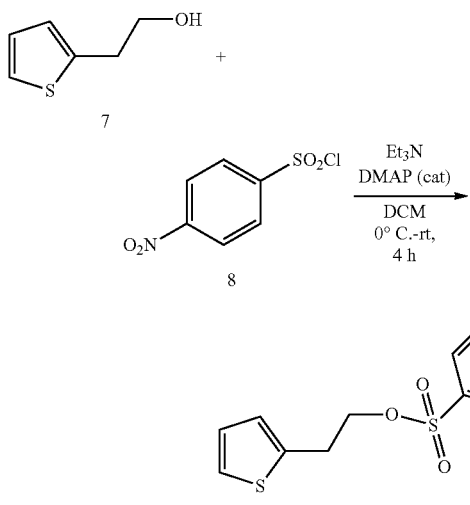

Thiopheneethanol (200.0 g; 1.56 moles; 1 equivalent), triethylamine (283 mL; 2.0 moles; 1.3 equivalents), 4-dimethylaminopyridine (DMAP) catalyst (2 g; 0.02 moles; 0.01 equivalent) and methylene chloride (1500 mL) were added to a 5.0 L, 4-necked round bottom flask equipped with overhead stirrer, temperature probe, N₂ inlet and addition funnel to form a reaction mixture.

The reaction mixture was cooled to 10° C. and 4-nitrobenzenesulfonyl chloride (415 g; 1.87 moles; 1.20 equivalents) was added as a slurry in methylene chloride (1000 mL) over a period of 2.0 hours, while keeping the reaction temperature below 15° C. Thereafter, under constant stirring, the reaction mixture was allowed to warm for 4 hours to room temperature. Yellow material precipitated from the solution, which was diluted with water (1000 mL) and stirred for 10 minutes. Two phases separated and additional water (1000 mL) was added and the mixture was stirred for 10 more minutes. The two phases that formed were separated and solvent was removed from the organic phase under reduced pressure to provide an orange solid as a crude 2-(2-thiophenylethyl) 4-nitro-benzene sulfonate 9 product (570 g; 116% wet yield; HPLC purity 93.8%).

To purify the crude product, 10 g of the solids were mixed with ethyl acetate (50 mL) and n-heptane (200 mL) and the mixture was heated at 48° C. to yield an almost clear solution (some non-dissolved dark solids were observed and were separated from the clear solution). The solution was allowed to warm to room temperature without stirring. Then, the solution was cooled in an ice-bath to 5° C. and held for 30 minutes. The light yellow crystals that formed were filtered and washed with n-heptane (30 mL) to yield 6.05 g (dried weight) of 2-(2-thiophenylethyl) 4-nitro-benzene sulfonate product 9 (60% yield; 99.9% HPLC purity).

Step-5: Synthesis of Compound 10

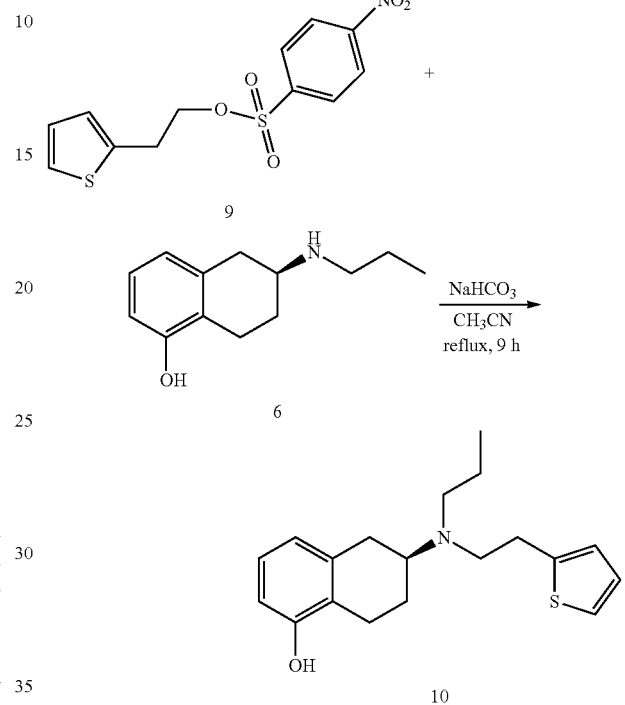

10 g of (S)-(−)-2-(N-propylamino)-5-hydroxytetraline, 6 were mixed with 9 g of NaHCO₃ (2.2 equivalents) and 16 g of 2-(2-thienyl)ethanol 2-nitrobenzenesulfonate 9 (1.05 equivalents) in 80 mL of acetonitrile. The mixture was refluxed for 9 hours, and then cooled and filtered for removal of suspended salts. 60 mL of water were added to the filtrate and concentrated by distillation for removal of acetonitrile. 40 mL of toluene were added and the layers were separated. The organic layer was twice washed with 10% NaHCO₃. Then, 50 mL of water and H₃PO₄ were added to pH=1-2. After layer separation, the aqueous acid layer was neutralized with 30% K₂CO₃ to pH=7-7.5 and extracted with 20 mL of ethyl acetate. The organic layer was washed with 10 mL of water, concentrated by distillation from the solvent to provide 10 g of compound as a white solid.

Step-6: Synthesis of Compound 12

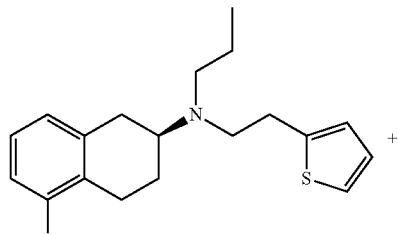

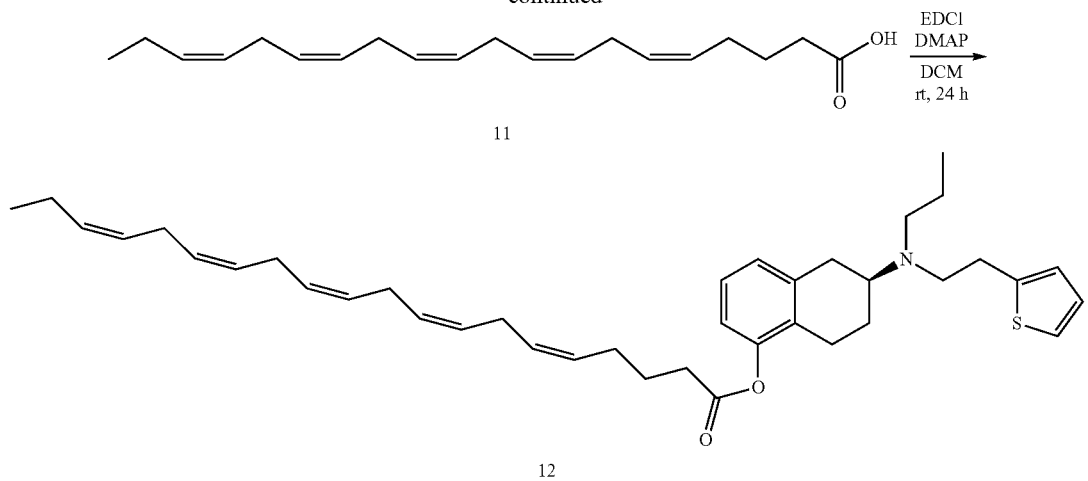

Stirring a mixture of a solution of compound 10 (18.0 mmol; 1.0 eq) and acid 11 (18.0 mmol; 1.0 eq) in Dichloromethane (DCM) (200 mL; LR grade); 1-ethyl-3-(3'-dimethylaminopropyl)carbodiimide.HCl (EDCI.HCl) (527.0 mmol; 1.5 eq) and 4-Dimethylaminopyridine (DMAP) (18.0 mmol; 1.0 eq) at room temperature (RT) for 24 hours. Reaction was monitored by TLC. On completion of the reaction, the reaction mixture was diluted with DCM (200 mL), washed with water (2×300 mL) followed by brine solution (300 mL) and dried over anhydrous $Na_2SO_4$ and evaporated under reduced pressure. The crude was purified by column chromatography over 100-200 mesh silica gel by using ethyl acetate-pet ether to yield compound 12. M.F: $C_{39}H_{53}NO_2S$; Mol. Wt.: 599.38; Elemental Analysis: C, 78.08; H, 8.90; N, 2.33; O, 5.33; S, 5.34.

EQUIVALENTS

The present disclosure provides among other things compositions and methods for treating neurologic diseases and their complications. While specific embodiments of the subject disclosure have been discussed, the above specification is illustrative and not restrictive. Many variations of the systems and methods herein will become apparent to those skilled in the art upon review of this specification. The full scope of the claimed systems and methods should be determined by reference to the claims, along with their full scope of equivalents, and the specification, along with such variations.

INCORPORATION BY REFERENCE

All publications and patents mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:
1. A compound of Formula I:

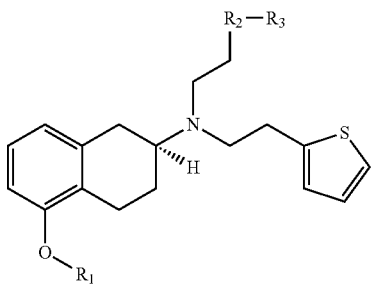

Formula I or a pharmaceutically acceptable salt, hydrate, polymorph, solvate, or stereoisomer thereof, wherein:
$R_1$ represents —$NH_2$,

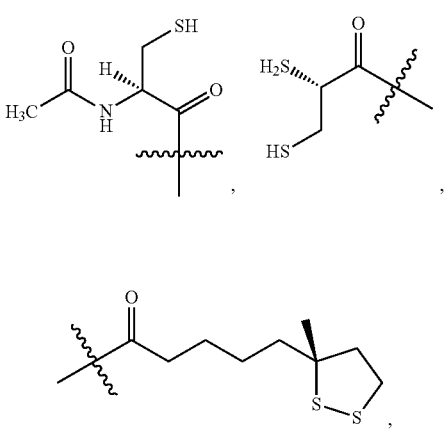

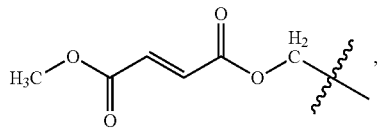

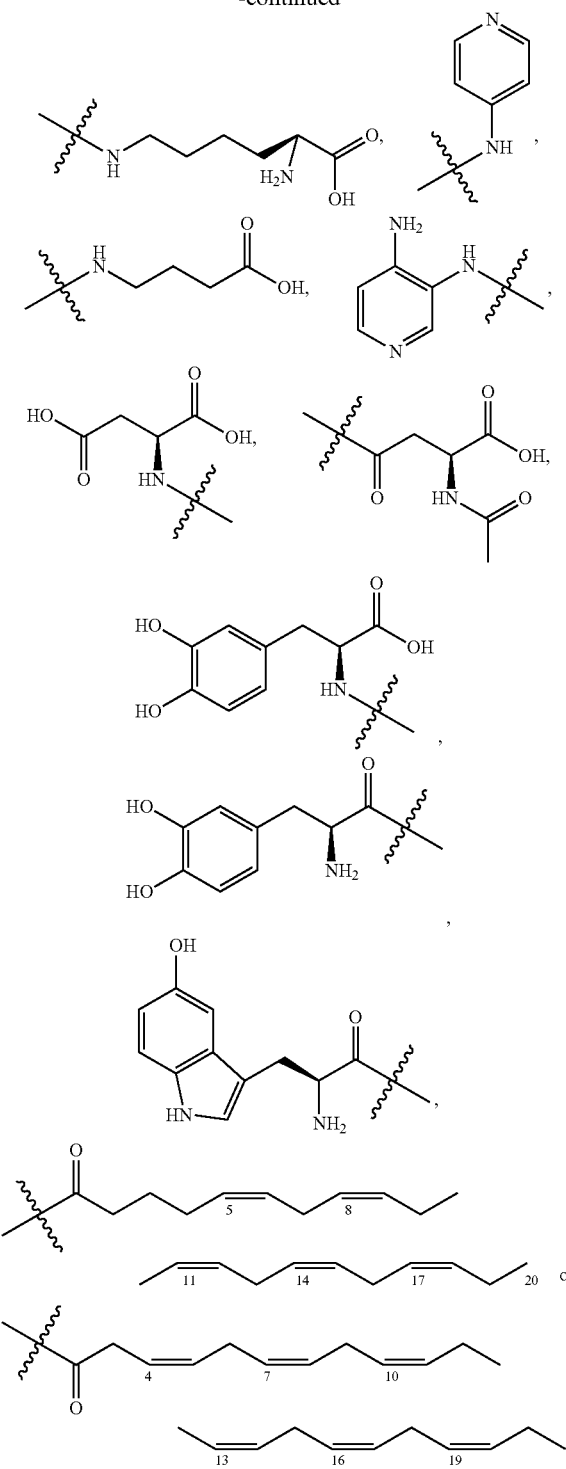
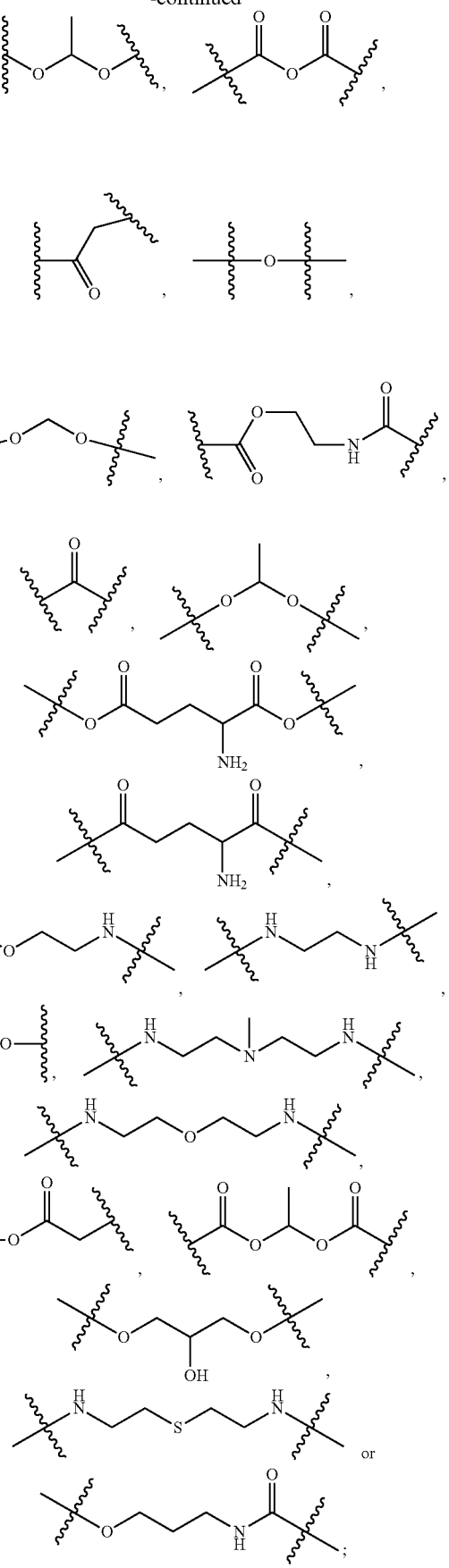
$R_2$ represents acetyl, $CH_3CO-$, $CH_3$,
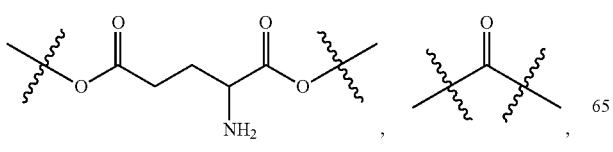

R₃ represents Null,
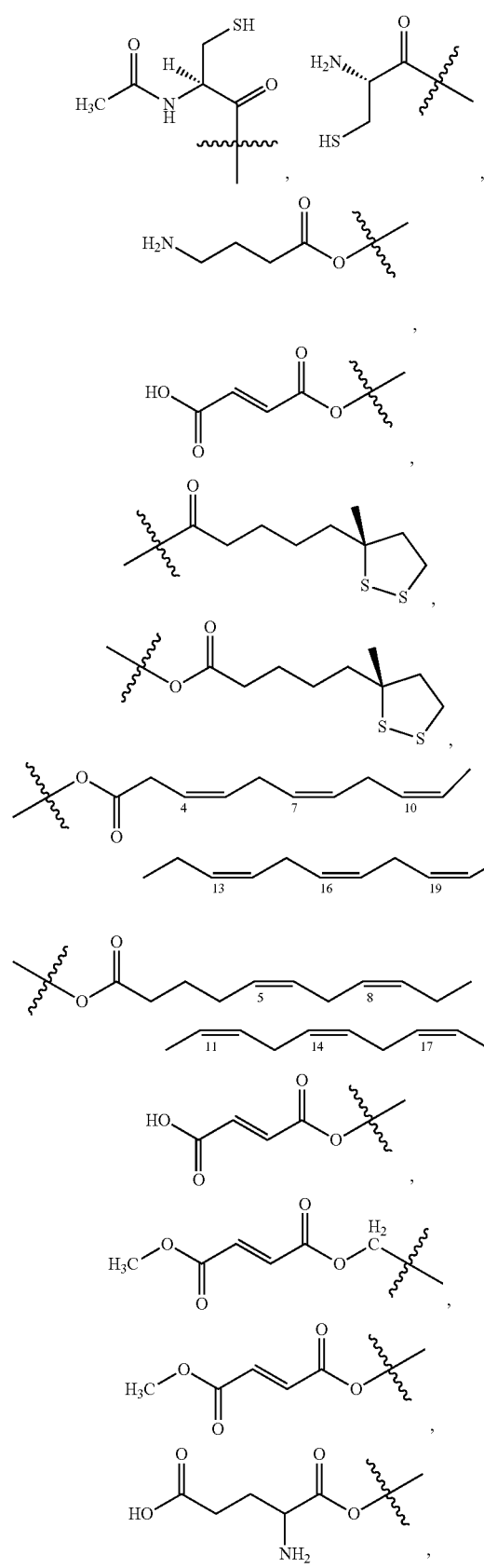
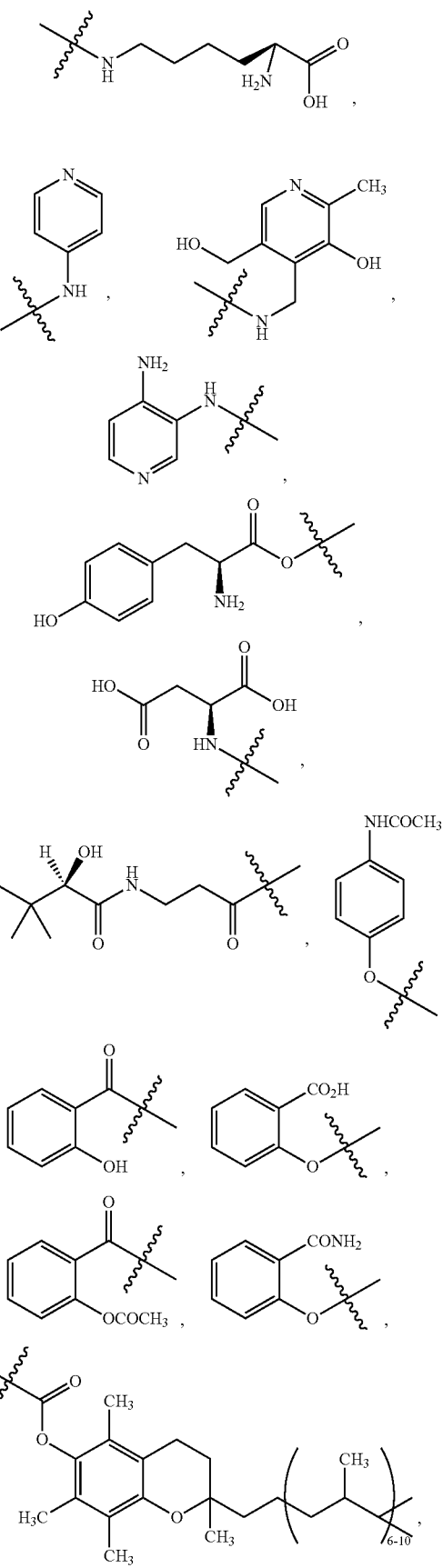

-continued

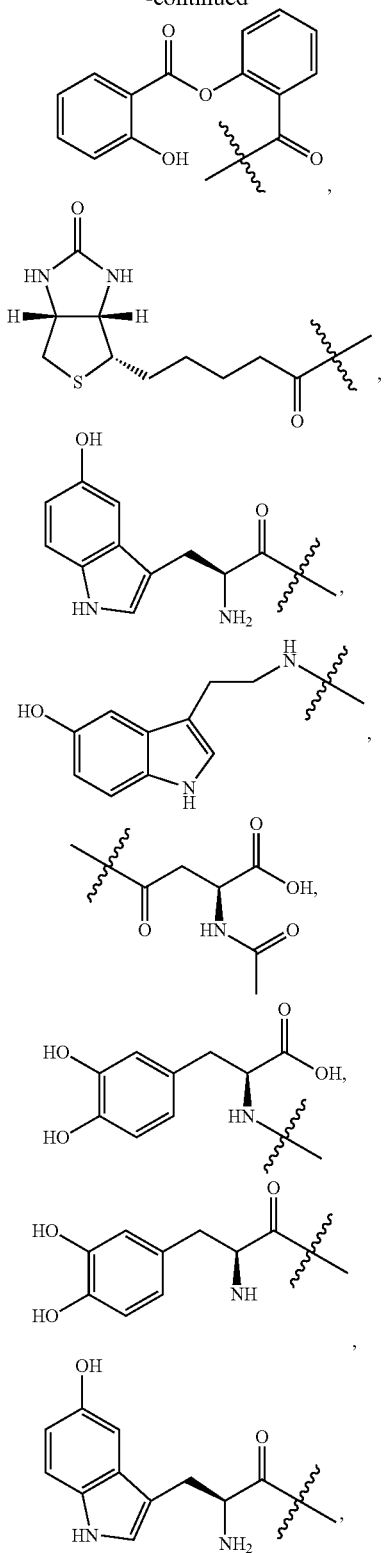

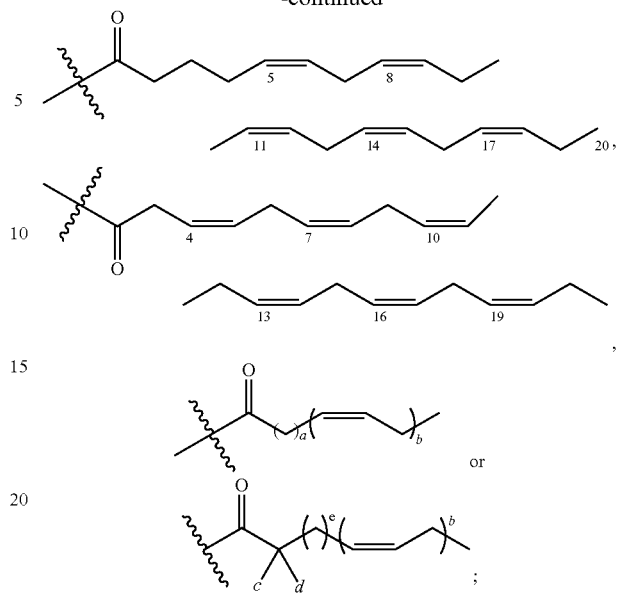

a is 2, 3 or 7;
each b is independently 3, 5 or 6;
e is 1, 2 or 6; and
c and d are each independently H, D, —OH, —OD, $C_1$-$C_6$-alkyl, —$NH_2$ or —$COCH_3$.

2. A pharmaceutical composition comprising a compound of claim 1 and a pharmaceutically acceptable carrier.

3. The pharmaceutical composition of claim 2, wherein said pharmaceutical composition is formulated for use by oral administration, delayed release or sustained release, transmucosal administration, syrup, topical administration, parenteral administration, injection, subdermal administration, oral solution, rectal administration, buccal administration or transdermal administration.

4. The pharmaceutical composition of claim 2, further comprising a molecular conjugate of rotigotine and carboxylic acid compounds selected from a group consisting of R-Lipoic acid, eicosapentaenoic acid, docosahexaenoic acid, fumaric acid and levodopa.

5. The pharmaceutical composition of claim 4, wherein the carboxylic acid compound is R-Lipoic acid.

6. The pharmaceutical composition of claim 4, wherein the carboxylic acid compound is eicosapentaenoic acid.

7. The pharmaceutical composition of claim 4, wherein the carboxylic acid compound is docosahexaenoic acid.

8. The pharmaceutical composition of claim 4, wherein the carboxylic acid compound is fumaric acid.

9. The pharmaceutical composition of claim 4, wherein the carboxylic acid compound is levodopa.

10. A method of treating a patient having a neurologic disease, wherein the method comprises administering to the patient an effective amount of the composition of claim 3, wherein the neurologic disease is depression, Alzheimer's disease, multiple sclerosis, Batten disease, Parkinson's disease, or restless legs syndrome.

* * * * *